(12) United States Patent
Sullivan et al.

(10) Patent No.: US 11,154,712 B2
(45) Date of Patent: Oct. 26, 2021

(54) METHODS FOR ASSESSING EFFICACY OF RENAL NEUROMODULATION AND ASSOCIATED SYSTEMS AND DEVICES

(71) Applicant: Medtronic Ardian Luxembourg S.a.r.l., Luxembourg (LU)

(72) Inventors: Carol Sullivan, Santa Rosa, CA (US); Stefan Tunev, Santa Rosa, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 128 days.

(21) Appl. No.: 15/506,740

(22) PCT Filed: Aug. 28, 2015

(86) PCT No.: PCT/US2015/047568
§ 371 (c)(1),
(2) Date: Feb. 26, 2017

(87) PCT Pub. No.: WO2016/033543
PCT Pub. Date: Mar. 3, 2016

(65) Prior Publication Data
US 2017/0347954 A1 Dec. 7, 2017

Related U.S. Application Data

(60) Provisional application No. 62/042,821, filed on Aug. 28, 2014.

(51) Int. Cl.
*A61B 5/00* (2006.01)
*A61B 5/20* (2006.01)
(Continued)

(52) U.S. Cl.
CPC ............ *A61N 1/3605* (2013.01); *A61B 5/201* (2013.01); *A61B 5/207* (2013.01); *A61B 5/4848* (2013.01);
(Continued)

(58) Field of Classification Search
CPC . A61B 10/0045; A61B 10/007; A61B 5/1405; A61B 5/201; A61B 18/1492;
(Continued)

(56) References Cited

U.S. PATENT DOCUMENTS 4,444,203 A 4/1984 Engelman et al.
4,602,624 A 7/1986 Naples et al.
(Continued)

FOREIGN PATENT DOCUMENTS

CN 101489624 7/2009
EP 1169976 1/2002
(Continued)

OTHER PUBLICATIONS

Extended European Search Report for App. No. 17208077.2, dated Jun. 4, 2018, 11 pages.
(Continued)

*Primary Examiner* — Eric D. Bertram
*Assistant Examiner* — Pamela M. Bays
(74) *Attorney, Agent, or Firm* — Shumaker & Sieffert, P.A.

(57) ABSTRACT

Provided herein are methods, devices and compositions for assessing neuromodulation efficacy based on changes in the level of one or more biomarkers in plasma or urine collected from a human subject following a renal neuromodulation procedure.

15 Claims, 3 Drawing Sheets

(51) Int. Cl.

| | | |
|---|---|---|
| *A61B 10/00* | (2006.01) | |
| *A61N 1/36* | (2006.01) | |
| *A61N 1/05* | (2006.01) | |
| *A61B 18/14* | (2006.01) | |
| *A61B 18/00* | (2006.01) | |
| *G01N 33/493* | (2006.01) | |
| *G01N 33/53* | (2006.01) | |
| *G01N 33/94* | (2006.01) | |
| *G01N 33/74* | (2006.01) | |
| *A61B 5/0538* | (2021.01) | |
| *A61B 5/145* | (2006.01) | |
| *A61B 5/24* | (2021.01) | |

(52) U.S. Cl.
CPC ........ *A61B 10/007* (2013.01); *A61B 18/1492* (2013.01); *A61N 1/0551* (2013.01); *A61N 1/36121* (2013.01); *G01N 33/493* (2013.01); *A61B 5/0538* (2013.01); *A61B 5/14507* (2013.01); *A61B 5/24* (2021.01); *A61B 5/4035* (2013.01); *A61B 5/4041* (2013.01); *A61B 2018/0022* (2013.01); *A61B 2018/00267* (2013.01); *A61B 2018/00345* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00702* (2013.01); *A61B 2018/00875* (2013.01); *A61B 2218/002* (2013.01); *A61N 1/36117* (2013.01); *G01N 33/5308* (2013.01); *G01N 33/74* (2013.01); *G01N 33/9433* (2013.01); *G01N 2800/347* (2013.01); *G01N 2800/52* (2013.01)

(58) Field of Classification Search
CPC .......... A61B 2018/00511; A61B 2018/00577; A61B 2018/00345; A61B 5/4848; A61B 5/207; A61N 1/0551; A61N 1/3605; A61N 1/36121; G01N 33/493
See application file for complete search history.

(56) References Cited

U.S. PATENT DOCUMENTS

| | | | |
|---|---|---|---|
| 4,649,936 | A | 3/1987 | Ungar et al. |
| 4,709,698 | A | 12/1987 | Johnston et al. |
| 4,764,504 | A | 8/1988 | Johnson et al. |
| 4,890,623 | A | 1/1990 | Cook et al. |
| 4,976,711 | A | 12/1990 | Parins et al. |
| 5,300,068 | A | 4/1994 | Rosar et al. |
| 5,301,683 | A | 4/1994 | Durkan |
| 5,358,514 | A | 10/1994 | Schulman et al. |
| 5,368,591 | A | 11/1994 | Lennox et al. |
| 5,423,744 | A | 6/1995 | Gencheff et al. |
| 5,484,400 | A | 1/1996 | Edwards et al. |
| 5,571,147 | A | 11/1996 | Sluijter et al. |
| 5,588,964 | A | 12/1996 | Imran et al. |
| 5,599,345 | A | 2/1997 | Edwards et al. |
| 5,608,519 | A | 3/1997 | Gourley et al. |
| 5,626,576 | A | 5/1997 | Janssen |
| 5,672,174 | A | 9/1997 | Gough et al. |
| 5,688,266 | A | 11/1997 | Edwards et al. |
| 5,700,282 | A | 12/1997 | Zabara |
| 5,707,400 | A | 1/1998 | Terry, Jr. et al. |
| 5,772,590 | A | 6/1998 | Webster, Jr. |
| 5,860,974 | A | 1/1999 | Abele |
| 5,865,787 | A | 2/1999 | Shapland et al. |
| 5,893,885 | A | 4/1999 | Webster, Jr. |
| 5,944,710 | A | 8/1999 | Dev et al. |
| 5,954,719 | A | 9/1999 | Chen et al. |
| 5,983,141 | A | 11/1999 | Sluijter et al. |
| 6,004,269 | A | 12/1999 | Crowley et al. |
| 6,009,877 | A | 1/2000 | Edwards |
| 6,024,740 | A | 2/2000 | Lesh et al. |
| 6,036,687 | A | 3/2000 | Laufer et al. |
| 6,066,134 | A | 5/2000 | Eggers et al. |
| 6,091,995 | A | 7/2000 | Ingle et al. |
| 6,099,524 | A | 8/2000 | Lipson et al. |
| 6,117,101 | A | 9/2000 | Diederich et al. |
| 6,135,999 | A | 10/2000 | Fanton et al. |
| 6,142,993 | A | 11/2000 | Whayne et al. |
| 6,149,620 | A | 11/2000 | Baker et al. |
| 6,161,048 | A | 12/2000 | Sluijter et al. |
| 6,219,577 | B1 | 4/2001 | Brown, III et al. |
| 6,224,592 | B1 | 5/2001 | Eggers et al. |
| 6,246,912 | B1 | 6/2001 | Sluijter et al. |
| 6,273,886 | B1 | 8/2001 | Edwards et al. |
| 6,283,951 | B1 | 9/2001 | Flaherty et al. |
| 6,292,695 | B1 | 9/2001 | Webster, Jr. et al. |
| 6,314,325 | B1 | 11/2001 | Fitz |
| 6,322,558 | B1 | 11/2001 | Taylor et al. |
| 6,322,559 | B1 | 11/2001 | Daulton et al. |
| 6,405,732 | B1 | 6/2002 | Edwards et al. |
| 6,413,255 | B1 | 7/2002 | Stern |
| 6,488,679 | B1 | 12/2002 | Swanson et al. |
| 6,506,189 | B1 | 1/2003 | Rittman, III et al. |
| 6,514,226 | B1 | 2/2003 | Levin et al. |
| 6,522,926 | B1 | 2/2003 | Kieval et al. |
| 6,542,781 | B1 | 4/2003 | Koblish et al. |
| 6,562,034 | B2 | 5/2003 | Edwards et al. |
| 6,616,624 | B1 | 9/2003 | Kieval |
| 6,622,731 | B2 | 9/2003 | Daniel et al. |
| 6,635,054 | B2 | 10/2003 | Fjield et al. |
| 6,640,120 | B1 | 10/2003 | Swanson et al. |
| 6,685,648 | B2 | 2/2004 | Flaherty et al. |
| 6,711,444 | B2 | 3/2004 | Koblish |
| 6,736,835 | B2 | 5/2004 | Pellegrino et al. |
| 6,752,805 | B2 | 6/2004 | Maguire et al. |
| 6,845,267 | B2 | 1/2005 | Harrison et al. |
| 6,850,801 | B2 | 2/2005 | Kieval et al. |
| 6,869,431 | B2 | 3/2005 | Maguire et al. |
| 6,885,888 | B2 | 4/2005 | Rezai |
| 6,893,436 | B2 | 5/2005 | Woodard et al. |
| 6,917,834 | B2 | 7/2005 | Koblish et al. |
| 6,923,808 | B2 | 8/2005 | Taimisto |
| 6,939,346 | B2 | 9/2005 | Kannenberg et al. |
| 6,949,097 | B2 | 9/2005 | Stewart et al. |
| 7,149,574 | B2 | 12/2006 | Yun et al. |
| 7,160,296 | B2 | 1/2007 | Pearson et al. |
| 7,162,303 | B2 | 1/2007 | Levin et al. |
| 7,221,979 | B2 | 5/2007 | Zhou et al. |
| 7,381,200 | B2 | 6/2008 | Katoh et al. |
| 7,390,894 | B2 | 6/2008 | Weinshilboum et al. |
| 7,617,005 | B2 | 11/2009 | Demarais et al. |
| 7,620,451 | B2 | 11/2009 | Demarais et al. |
| 7,647,115 | B2 | 1/2010 | Levin et al. |
| 7,653,438 | B2 | 1/2010 | Deem et al. |
| 7,717,948 | B2 | 5/2010 | Demarais et al. |
| 7,778,703 | B2 | 8/2010 | Gross et al. |
| 8,131,371 | B2 | 3/2012 | Demarals et al. |
| 8,131,372 | B2 | 3/2012 | Levin et al. |
| 8,140,170 | B2 | 3/2012 | Rezai et al. |
| 8,145,317 | B2 | 3/2012 | Demarais et al. |
| 8,150,518 | B2 | 4/2012 | Levin et al. |
| 8,150,519 | B2 | 4/2012 | Demarais et al. |
| 8,150,520 | B2 | 4/2012 | Demarais et al. |
| 8,175,711 | B2 | 5/2012 | Demarais et al. |
| 8,702,619 | B2 | 4/2014 | Wang |
| 8,768,470 | B2 | 7/2014 | Deem et al. |
| 8,909,316 | B2 | 12/2014 | Ng |
| 8,977,359 | B2 | 3/2015 | Rossing |
| 9,002,446 | B2 | 4/2015 | Wenzel et al. |
| 9,014,809 | B2 | 4/2015 | Wenzel et al. |
| 9,014,821 | B2 | 4/2015 | Wang |
| 9,022,948 | B2 | 5/2015 | Wang |
| 9,043,191 | B2 | 5/2015 | Grady et al. |
| 9,119,600 | B2 | 9/2015 | Richardson et al. |
| 9,168,094 | B2 | 10/2015 | Lee et al. |
| 9,179,973 | B2 | 11/2015 | Nabutovsky et al. |
| 9,186,212 | B2 | 11/2015 | Nabutovsky et al. |
| 9,295,842 | B2 | 3/2016 | Ghaffari et al. |
| 9,314,300 | B2 | 4/2016 | Nabutovsky et al. |

(56) References Cited

U.S. PATENT DOCUMENTS

| | | | |
|---|---|---|---|
| 9,375,154 B2 | 6/2016 | Wang | |
| 9,427,283 B2 | 8/2016 | Nabutovsky et al. | |
| 9,427,579 B2 | 8/2016 | Fain et al. | |
| 9,554,850 B2 | 1/2017 | Lee et al. | |
| 9,579,030 B2 | 2/2017 | Scheuermann et al. | |
| 2002/0087208 A1 | 7/2002 | Koblish et al. | |
| 2002/0107515 A1 | 8/2002 | Edwards et al. | |
| 2002/0139379 A1 | 10/2002 | Edwards et al. | |
| 2002/0165532 A1 | 11/2002 | Hill et al. | |
| 2002/0183682 A1 | 12/2002 | Darvish et al. | |
| 2003/0050635 A1 | 3/2003 | Truckai et al. | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0125790 A1 | 7/2003 | Fastovsky et al. | |
| 2003/0181897 A1 | 9/2003 | Thomas et al. | |
| 2003/0195507 A1 | 10/2003 | Stewart et al. | |
| 2003/0199863 A1 | 10/2003 | Swanson et al. | |
| 2003/0216792 A1 | 11/2003 | Levin et al. | |
| 2003/0229340 A1 | 12/2003 | Sherry et al. | |
| 2003/0233099 A1 | 12/2003 | Danaek et al. | |
| 2004/0010289 A1 | 1/2004 | Biggs et al. | |
| 2004/0116401 A1* | 6/2004 | Shah | A61K 31/16 514/183 |
| 2004/0167509 A1 | 8/2004 | Taimisto | |
| 2004/0215186 A1 | 10/2004 | Cornelius et al. | |
| 2005/0080409 A1 | 4/2005 | Young et al. | |
| 2005/0096647 A1 | 5/2005 | Steinke et al. | |
| 2005/0153379 A1 | 7/2005 | Hoon et al. | |
| 2005/0187579 A1 | 8/2005 | Danek et al. | |
| 2005/0228460 A1 | 10/2005 | Levin et al. | |
| 2006/0085054 A1 | 4/2006 | Zikorus et al. | |
| 2006/0095029 A1 | 5/2006 | Young et al. | |
| 2006/0206150 A1 | 9/2006 | Demarais et al. | |
| 2006/0212076 A1 | 9/2006 | Demarais et al. | |
| 2006/0271111 A1 | 11/2006 | Demarais et al. | |
| 2007/0129720 A1 | 6/2007 | Demarais et al. | |
| 2007/0135875 A1 | 6/2007 | Demarais et al. | |
| 2007/0265687 A1 | 11/2007 | Deem et al. | |
| 2008/0057590 A1 | 3/2008 | Urdea et al. | |
| 2008/0161228 A1* | 7/2008 | Ryals | G01N 33/5008 702/19 |
| 2008/0319513 A1 | 12/2008 | Pu et al. | |
| 2009/0024195 A1 | 1/2009 | Rezai et al. | |
| 2009/0036948 A1 | 2/2009 | Levin et al. | |
| 2009/0105605 A1 | 4/2009 | Abreu | |
| 2010/0016929 A1* | 1/2010 | Prochazka | A61N 1/36021 607/72 |
| 2010/0069888 A1 | 3/2010 | Solomon | |
| 2010/0086948 A1 | 4/2010 | Gold et al. | |
| 2010/0087716 A1 | 4/2010 | Nashed | |
| 2010/0114244 A1 | 5/2010 | Manda et al. | |
| 2010/0137860 A1 | 6/2010 | Demarais et al. | |
| 2010/0137952 A1 | 6/2010 | Demarais et al. | |
| 2010/0166739 A1 | 7/2010 | Chancellor et al. | |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2010/0280562 A1* | 11/2010 | Pi | C12Q 1/6883 607/2 |
| 2010/0331833 A1 | 12/2010 | Maschke et al. | |
| 2011/0060324 A1 | 3/2011 | Wu et al. | |
| 2011/0112400 A1 | 5/2011 | Emery et al. | |
| 2011/0152759 A1 | 6/2011 | Clymer et al. | |
| 2011/0160644 A1 | 6/2011 | Dacey, Jr. et al. | |
| 2011/0178570 A1* | 7/2011 | Demarais | A61N 1/05 607/44 |
| 2011/0184337 A1 | 7/2011 | Evans et al. | |
| 2011/0208096 A1 | 8/2011 | Demarais et al. | |
| 2011/0270120 A1 | 11/2011 | McFarlin et al. | |
| 2011/0306851 A1 | 12/2011 | Wang | |
| 2012/0029504 A1 | 2/2012 | Afonso et al. | |
| 2012/0116383 A1 | 5/2012 | Mauch et al. | |
| 2012/0123400 A1 | 5/2012 | Francischelli et al. | |
| 2012/0130289 A1 | 5/2012 | Demarais et al. | |
| 2012/0130345 A1 | 5/2012 | Levin et al. | |
| 2012/0143097 A1 | 6/2012 | Pike, Jr. | |
| 2012/0172837 A1 | 7/2012 | Demarais et al. | |
| 2012/0172870 A1 | 7/2012 | Jenson et al. | |
| 2012/0191079 A1 | 7/2012 | Moll et al. | |
| 2012/0296232 A1 | 11/2012 | Ng | |
| 2012/0296329 A1 | 11/2012 | Ng | |
| 2013/0172878 A1 | 7/2013 | Smith | |
| 2013/0178750 A1 | 7/2013 | Sheehan et al. | |
| 2013/0218029 A1 | 8/2013 | Cholette et al. | |
| 2013/0237948 A1 | 9/2013 | Donders et al. | |
| 2013/0245726 A1 | 9/2013 | Zarins | |
| 2013/0274614 A1 | 10/2013 | Shimada et al. | |
| 2013/0282001 A1 | 10/2013 | Hezi-Yamit et al. | |
| 2013/0289358 A1* | 10/2013 | Melsky | A61B 18/24 600/249 |
| 2013/0289369 A1 | 10/2013 | Margolis | |
| 2014/0012133 A1 | 1/2014 | Sverdlik et al. | |
| 2014/0066803 A1 | 3/2014 | Choi | |
| 2014/0073903 A1 | 3/2014 | Weber et al. | |
| 2014/0074089 A1 | 3/2014 | Nishii | |
| 2014/0128865 A1 | 5/2014 | Gross | |
| 2014/0180273 A1* | 6/2014 | Nair | A61B 8/12 606/34 |
| 2014/0213873 A1 | 7/2014 | Wang | |
| 2014/0221805 A1 | 8/2014 | Wang | |
| 2014/0236137 A1 | 8/2014 | Tran et al. | |
| 2014/0236138 A1 | 8/2014 | Tran et al. | |
| 2014/0246465 A1 | 9/2014 | Peterson et al. | |
| 2014/0249524 A1 | 9/2014 | Kocur | |
| 2014/0266235 A1 | 9/2014 | Mathur | |
| 2014/0275924 A1 | 9/2014 | Min et al. | |
| 2014/0276124 A1 | 9/2014 | Cholette et al. | |
| 2014/0276733 A1 | 9/2014 | Vanscoy et al. | |
| 2014/0276755 A1 | 9/2014 | Cao et al. | |
| 2014/0276762 A1 | 9/2014 | Parsonage | |
| 2014/0276766 A1 | 9/2014 | Brotz et al. | |
| 2014/0276767 A1 | 9/2014 | Brotz et al. | |
| 2014/0276773 A1 | 9/2014 | Brotz et al. | |
| 2014/0316400 A1 | 10/2014 | Blix et al. | |
| 2014/0316496 A1 | 10/2014 | Masson et al. | |
| 2014/0330267 A1 | 11/2014 | Harrington | |
| 2014/0336637 A1 | 11/2014 | Agrawal et al. | |
| 2015/0005764 A1 | 1/2015 | Hanson et al. | |
| 2015/0018656 A1 | 1/2015 | Min et al. | |
| 2015/0025524 A1 | 1/2015 | Nabutovsky | |
| 2015/0112329 A1 | 4/2015 | Ng | |
| 2015/0119674 A1 | 4/2015 | Fischell et al. | |
| 2015/0173673 A1 | 6/2015 | Toth et al. | |
| 2015/0201997 A1 | 7/2015 | Osypka | |
| 2015/0216590 A1 | 8/2015 | Wang et al. | |
| 2015/0223877 A1 | 8/2015 | Behar et al. | |
| 2015/0224326 A1 | 8/2015 | Toth et al. | |
| 2015/0289929 A1 | 10/2015 | Toth et al. | |
| 2015/0366609 A1 | 12/2015 | Richardson et al. | |
| 2016/0000345 A1 | 1/2016 | Kobayashi et al. | |
| 2016/0029960 A1 | 2/2016 | Toth et al. | |
| 2016/0038028 A1 | 2/2016 | Buelna et al. | |
| 2016/0081744 A1 | 3/2016 | Wang | |
| 2016/0106498 A1 | 4/2016 | Highsmith et al. | |
| 2016/0184010 A1 | 6/2016 | Nabutovsky et al. | |
| 2016/0213262 A1 | 7/2016 | Ghaffari et al. | |
| 2016/0213424 A1 | 7/2016 | Ghaffari et al. | |
| 2016/0324572 A1 | 11/2016 | Gross et al. | |
| 2016/0331451 A1 | 11/2016 | Nabutovsky et al. | |
| 2016/0331453 A1 | 11/2016 | Fain et al. | |
| 2016/0374568 A1 | 12/2016 | Wang | |
| 2017/0215950 A1 | 8/2017 | Gross et al. | |

FOREIGN PATENT DOCUMENTS

| | | | |
|---|---|---|---|
| EP | 2316371 | A1 | 5/2011 |
| EP | 2594193 | A2 | 5/2013 |
| EP | 2613704 | A2 | 7/2013 |
| EP | 2709517 | A1 | 3/2014 |
| EP | 2747691 | A1 | 7/2014 |
| EP | 2797535 | A1 | 11/2014 |
| EP | 2852339 | | 4/2015 |

(56) References Cited

FOREIGN PATENT DOCUMENTS

| | | |
|---|---|---|
| EP | 2866645 | 5/2015 |
| EP | 2887900 | 7/2015 |
| EP | 2907464 | 8/2015 |
| EP | 2914334 | 9/2015 |
| EP | 2967383 | 1/2016 |
| EP | 2978372 | 2/2016 |
| EP | 3011899 | 4/2016 |
| EP | 3028628 | 6/2016 |
| EP | 3089686 | 11/2016 |
| JP | H08504531 | 5/1996 |
| JP | H1071037 | 3/1998 |
| JP | 2001518808 | 10/2001 |
| JP | 2005278739 | 10/2005 |
| JP | 2008-515544 | 5/2008 |
| JP | 2009539565 | 11/2009 |
| JP | 2010162163 | 7/2010 |
| JP | 2010533513 | 10/2010 |
| JP | 2011505929 | 3/2011 |
| WO | WO-2014091328 A1 | 7/1989 |
| WO | WO-1994/007446 A1 | 4/1994 |
| WO | WO-1995/025472 A1 | 9/1995 |
| WO | WO-1995/031142 A1 | 11/1995 |
| WO | WO-1997/036548 A1 | 10/1997 |
| WO | WO-1998/042403 A1 | 10/1998 |
| WO | WO-1999/000060 A1 | 1/1999 |
| WO | WO-19990000060 | 1/1999 |
| WO | WO-2011/022897 A1 | 4/2001 |
| WO | WO-2001/070114 A1 | 9/2001 |
| WO | WO-2003/022167 | 3/2003 |
| WO | WO-2003/082080 | 10/2003 |
| WO | WO-2005/030072 A1 | 4/2005 |
| WO | WO-2005/41748 A2 | 5/2005 |
| WO | WO-2005/110528 A1 | 11/2005 |
| WO | WO-2006/041881 A2 | 4/2006 |
| WO | WO-2006041881 A2 | 4/2006 |
| WO | WO-2006/105121 A2 | 10/2006 |
| WO | WO-2007/008954 A2 | 1/2007 |
| WO | WO-2007/078997 A2 | 7/2007 |
| WO | WO-2008003058 | 1/2008 |
| WO | WO-2008/049084 A2 | 4/2008 |
| WO | WO-2010078175 A1 | 7/2010 |
| WO | WO-2011089935 | 7/2011 |
| WO | WO-2012024543 | 2/2012 |
| WO | WO-2012033974 A2 | 3/2012 |
| WO | WO-2012068471 A1 | 5/2012 |
| WO | WO-2012158864 A1 | 11/2012 |
| WO | WO-2013030738 A1 | 3/2013 |
| WO | WO-2013030743 A1 | 3/2013 |
| WO | WO-2013074813 | 5/2013 |
| WO | WO-2013101485 | 7/2013 |
| WO | WO-2013112844 A2 | 8/2013 |
| WO | WO-2014012282 A1 | 1/2014 |
| WO | WO-2014029355 A1 | 2/2014 |
| WO | WO-2014059165 A2 | 4/2014 |
| WO | WO-2014068577 A2 | 5/2014 |
| WO | WO-2014091401 | 6/2014 |
| WO | WO-2014149550 A2 | 9/2014 |
| WO | WO-2014149552 A1 | 9/2014 |
| WO | WO-2014149553 A1 | 9/2014 |
| WO | WO-2014149690 A2 | 9/2014 |
| WO | WO-2014150425 A1 | 9/2014 |
| WO | WO-2014150432 A1 | 9/2014 |
| WO | WO-2014150441 A2 | 9/2014 |
| WO | WO-2014150455 A1 | 9/2014 |
| WO | WO-2014158708 A1 | 10/2014 |
| WO | WO-2014158713 A1 | 10/2014 |
| WO | WO-2014163990 A1 | 10/2014 |
| WO | WO-2014179768 A1 | 11/2014 |
| WO | WO-2014182946 A2 | 11/2014 |
| WO | WO2016/033543 | 3/2016 |

OTHER PUBLICATIONS

Centi et al., "Strategies for electrochemical detection in immunochemistry," Bioanalysis, vol. 1, No. 7, Oct. 2009, pp. 1271-1291.
Padfield et al., "Changes of Vasopressin in Hypertension: Cause or Effect?" The Lancet, vol. 307, Issue 7972, Jun. 12, 1976, pp. 1255-1257.
Rusling et al., "Measurement of biomarker proteins for point-of-care early detection and monitoring of cancer," Analyst, vol. 135, Apr. 5, 2010, pp. 2496-2511.
Zhang et al., "Neuropeptide Y Promoter Polymorphism Modifies Effects of a Weight-Loss Diet on 2-Year Changes of Blood Pressure: The Preventing Overweight Using Novel Dietary Strategies Trial", Hypertension, vol. 60, Nov. 2012, pp. 1169-1175, DOI:10.1161/HYPERTENSIONAHA.112.197855.
Chinushi et al., "Blood Pressure and Autonomic Responses to Electrical Stimulation of the Renal Arterial Nerves Before and After Ablation of the Renal Artery." Hypertension, 2013, 61, pp. 450-456.
Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.
Böhm M, Mahfoud F, Ukena C, Hoppe UC, Narkiewicz K, Negoita M, Ruilope L, Schlaich MP, Schmieder RE, Whitbourn R, Williams B, Zeymer U, Zirlik A, Mancia G; "GSR Investigators First report of the Global Symplicity Registry on the effect of renal artery denervation in patients with uncontrolled hypertension." Hypertension. Apr. 2015;65(4):766-74.
Soulis JV1, Fytanidis DK1, Seralidou KV1, Giannoglou GD2, "Wall shear stress oscillation and its gradient in the normal left coronary artery tree bifurcations" HIPPOKRATIA 2014, 18, 1: 12-16.
Knight et al., "Choosing the optimal wall shear parameter for the prediction of plaque location—A patient-specific computational study in human right coromary arteries." Elsevier Inc., Aug. 2010, vol. 211, Issue 2, pp. 445-450.
International Search Report and Written Opinion for International App. No. PCT/US2013/030041, dated Sep. 23, 2013, 20 pages.
Abruzzo, Provvidenza et al., "Oxidative strss in the denervated muscle," Free Radical Research, vol. 44, No. 5, 2010, 563-576.
Amsellem S. et al., "Cubilin Is Essential for Albumin Reabsorption in the Renal Proximal Tubule," J Am Soc Nephril, vol. 21, 2010,1859-1867.
Andres, Vicente, "Control of vascular cell proliferation and migration by cyclin-dependent kinase signalling: new perspectives and therapeutic potential," Cardiovascular Research, vol. 63, 2004, 11 pages.
Ankri, R. et al., "In-vivo Tumor detection using diffusion reflection measurements of targeted gold nanorods—a quantitative study," Biophotonics, 2012, 11 pages.
Bengatta, S. et al., "MMP9 and SCF Protect from Apoptosis in Acute Kidney Injury," J Am Soc Nephril, vol. 20, 2009, 787-797.
Bhattacharya, S. et al. "Role of p38 Protein Kinase in the Ligand-independent Ubiquitination and Down-regulation of the IFNAR1 Chain of Type I Interferon Receptor," The Journal of Biological Chemistry, vol. 286 No. 25, 2011, 22069-22076.
Bisoffi, M. et al., "Detection of viral bioagents using a shear horizontal surface acoustic wave biosensor," Biosensors and Bioelectronics, vol. 23, 2008, 7 pages.
Centi et al., "Strategies for electrochemical detection in Immunochemistry," Bioanalysis, vol. 1. No. 7, 2009, 21 pages.
Dange, M. et al., "Each Conserved Active Site Tyr in the Three Subunits of Human Isocitrate Dehydrogenase Has a Different Function," The Journal of Biological Chemistry, vol. 285, No. 27, 2010, 6 pages.
Darisipudi, M. et al., "Dual Blockade of the Homeostatic Chemokine CXCL 12 and the Proinflammatory Chemokine CCL2 Has Addictive Protective Effects on Diabetic Kidney Disease," The American Journal of Pathology, vol. 179, No. 1, 2011, 9 pages.

(56) References Cited

OTHER PUBLICATIONS

Dhruvajyoti, Roy et al., ""Seeing and Counting" Individual antigens Captured on a Microarrayed Soit with Force-Based Atomic Force Microscopy," Anal. Chem. vol. 82, 2010 6 pages.

Dikow, Ralf et al., "In Renal Transplants With Delayed Graft Function Chemokines and Chemokine Receptor Expression Predict Long-Term Allograft Function," Transplantation, vol. 90, 2010, 71-776.

Dinish, U. et al., "Highly sensitive SERS detection of cancer proteins in low sample volume using hollow core photonic crystal fiber," Biosens, Bioelecton, 2012, 6 pages.

Dorr et al., "Soluble fms-Like Tyrosine Kinase-1 and Endothelial Adhesion Molecules (Intercellular Cell Adhesion Molecule-1 and Vascular Cell Adhesion Molecule-1) as Predictive Markers for Blood Pressure Reduction After Renal Sympathetic Denervation." Hypertension, 2014, 63, pp. 984-990.

Ford. M. et al., "Expression of fibroblast growth factors and their receptors in rat glomeruli," Kidney International, vol. 51, 1997, 10 pages.

Fragiadaki, Maria et al., "Interstitial fibrosis is associated with increased COL1A2 transcription in AA-injured renal tubular epithelial cells in vivo," Matrix Biology, vol. 30, 2011, 396-403.

Frostick, S. et al., "Schwann Cells, Neurotrophic Factors, and Peripheral Nerve Regeneration," Microsurgery, vol. 18, 1998, 9 pages.

Gaikwad, A. et al., "Epigenetic changes and alteration of Fbn1 and Col3A1 gene expression under hyperglycaemic and hyperinsulinaemic conditions," Biochem. J., vol. 432, 2010, 10 pages.

Green, H., et al., "Development of ERK Activity Sensor, an in vitro, FRET-based sensor of Extracellulat Regulated Kinase activity," BMC Chemical Biology, vol. 5, No. 1, 2005, 8 pages.

Grishman, Ellen et al., "'Toil-like receptors, the NLRP3 inflammasome, and interleukin-1β in the development and progression of type 1 diabetes," Pediatric Research, vol. 71, No. 6, 2012, 7 pages.

Heberlein, Annemarie et al., BDNF plasma levels decrease during benzodiazepine withdrawal in patients suffering from comorbidity of depressive disorder and benzodiazepine dependence, Psychopharmacology, vol. 209, 2010, 3 pages.

Hervas, M. et al., "Electrochemical immunosensing on board microfluidic chip platforms," Trends in Analytical Chemistry, vol. 31, 2012, 20 pages.

Higgins, J, et al., "Gene Expression in the Normal Adult Human Kidney Assessed by Complementary DNA Microarray," Molecular Biology of the Cell, vol. 15, 2004, 649-656.

Hirst, E., "Bond-rupture immunosensors—A review," Biosensors and Bioelectronics, vol. 23, 2008, 10 pages.

Horke, S. et al,, "Paraoxonase-2 Reduces Oxidative Stress in Vascular Cells and Decreases Endoplasmic Reticulum Stress-Induced Caspase Activation," Circulation, vol. 115, 2007, 11 pages.

Ihling, C. et al., "Endothelin-1 and Endothelin Converting Enzyme-1 in Human Atherosclerosis-Novel Targets for Pharrnacotherapy in Atherosclerosis," Current Vascular Pharmacology, vol. 2, 2004, 10 pages.

Jacobs, C. et al., " Review: Carbon nanotube based electrochemical sensors for biomolecules," Analytical Chimica Acta, vol. 662, 2010, 23 pages.

Jin, Xinghua et al., "Delineation of apoptotic genes for synergistic apoptosis of lexatumumab and anthracyclines in human renal cell carcinoma cells by polymerase chain reaction array," Anti-Cancer Drugs, vol. 23, No. 4, 2012, 10 pages.

Johnson, B. et al., "Biosensing using dynamic-mode cantilever sensors: A review," Biosensors arid Bioelectronics, vol. 32, 2012, 18 pages.

Kasuno, Kenji et al., "Clinical Application of Urinary Redox Regulating Protein," Thioredoxin, Rinsho Byori, vol. 59, 2011, 189-195.

Kerr, Heather et al., "Complement-mediated injury and protection of enforhelium: Lessons from atypical haemolytic uraemic syndrome," Immunobiology, vol. 217, 2012, 195-203.

Kinoshita, Yukiko et al., "Angiotensin II type I receptor blockade suppresses glomerular renin-angiotensin system activation,; oxidative stress, and progressive glomerular injury in rat anti-glomerular basement membrane; glomerulonephritis," Translational Research, vol. 158, No. 4, 2011, 15 pages.

Klosterhalfen, B. et al., "Influence of Heat Shock Protein 70 and Metallothionein Induction by Zinc-bis-(DL-Hydrogenaspartate) on the Release of Inflammatory Mediators in a Porcine Model of Recurrent Endotoxemia." Biochemical Pharmacology, vol. 52, 1996, 1201-1210.

Kopp, "Endothelin in the Control of Renal Sympathetic Nerve Activity," Contrib Nephrol. Basel, Karger, vol. 172, 2011, 107-119.

Kopp, Ulla C. et al., "Impaired Interaction Between Efferent and Afferent Renal Nerve Activity in SHR Involves Increased Activation of α2-Adrenoceptors," vol. 57, 2011, 640-647.

Kourtzelis, L., et al., "Complement anaphylatoxin C5a contributes to hemodialysis-associated thrombosis," Blood, 116, No. 4, 2010 9 pages.

Krukoff, Teresa L. et al., "Effects of renal denervation and reinnervation on ganglionic gene; expression of neurotransmitter proteins and c-fos in rat," Molecular Brain Research, vol. 19, 1993, 6 pages.

Lan, Hui Yao, Transforming growth factor-β/Smad signalling in diabetic nephropathy, Clinical and Experimental Pharmacology and Physiology, vol. 39, 2012, 731-738.

Lantero, A. et al., "Transforming Growth Factor-β in Normal Nociceptive Processing and Pathological Pain Models," Mol Neurobiol, vol. 45, 2012, 76-86.

Lechner, Stefan et al., "Regulation of neuronal ion channels via P2Y receptors" Purinergic Signalling, vol. 1, 2004, 31-41.

Lee, Y. et al., "Fibromodulin Suppresses Nuclear Factor-κB Activity by Inducing the Delayed Degradation of IKBA via a JNK-dependent Pathway Coupled to Fibroblast Apoptosis," The Journal of Biological Chemistry, vol. 286, No. 8, 2011, 9 pages.

Leguillon-Buffello, D. et al., "An Alternative Quantitative Acoustical and Electrical Method for Detection of Cell Adhesion Process in Real-Time," Biotechnology and Bioengineering, vol. 108, No. 4, 2011, 16 pages.

Leonard, M., et al., "Reoxygenation-specific activation of the antioxidant transcription factor Nrf2 mediates cytoprotective gene expression in ischemia-reperfusion injury," The FASEB Journal, vol. 20, 2006, 3 pages.

Liang, W. et al., "A novel rnicrofluidic immunoassay system based on electrochemical immunosensors: An application for the detection of NT-proBNP in whole blood," Biosensors and Bioelectronics, vol. 31, 2012, 6 pages.

Liu, Bin et al., "Role of cyclooxygenase-1-mediated prostacyclin synthesis in endothelium-dependent vasoconstrictor activity of porcine interlobular renal arteries," Am J Physiol Renal Physiol, vol. 302, 2012, F1133-F1140.

Liu, Y, et al., "BID Binds to Replication Protein A and Stimulates ATR Function following Replicative Stress," Molecular and Cellular Biology, vol. 31, No. 21, 2011, 12 pages.

Liu, Yanxin et al,, "A novel SNP of the ATP1A1 gene is associated with heat tolerance traits in dairy cows," vol. 38, 2011, 83-88.

Liu, Ying et al., "Induction of KLF4 in response to heat stress," Cell Stress & Champerones, vol. 11, No. 4, 2006, 379-389.

Liu, Yong et al., "Renal Medullary MicroRNAs in Dahl Salt-Sensitive Rats: miR-29b Regulates Several Collagens and Related Genes," Hypertension, vol. 55, 2010, 974-982.

Lloyd-Burton, S. et al., "SPARC-Like 1 (SC1) Is a Diversely Expressed and Developmentally Regulated Matricellular Protein That Does Not Compensate for the Absence of SPARC in the CNS," The Journal of Comparative Neurology: Research in Systems Neuroscience, vol. 520, 2012, 2575-2590

Lo, Denise et al., "Chemokines and their Receptors in Human Renal Allotransplantation," Transplantation, Author manuscript; available in PMC, 2012, 14 pages.

Longley, C. D. et al., "Proportions of Renal and Splenic Postganglionic Sympathetic Populations Containing Galanin and Dopamine Beta Hydroxylase," Neuroscience, vol. 55, No. 1, 1993, 9 pages.

(56) References Cited

OTHER PUBLICATIONS

Lu, X. et al., "The Role of Heat Shock Protein (HSP) in Atherosclerosis: Pathophysiology; and Clinical Opportunities," Current Medicinal Chemistry, vol. 17, 2010, 957-973.

Luo, Lin, "Gene expression profiles of laser-captured adjacent neuronal subtypes," Nature Medicine, vol. 5, No. 1, 1999, 6 pages.

Ma Frank, et al., "TGF-β1-activated kinase-1 regulated inflammation and fibrosis in the obstructed kidney," Am J. Physiol Renal Physiol, vol. 300, 2011, 12 pages.

Maeshima, A. et al., "Activin A: Autocrine Regulator of Kidney Development and Repair," Endocrine Journal, vol. 55, No. 1, 2008 9 pages.

Maity, Tapan et al., "Distinct, Gene Specific Effect of Heat Shock on Heat Shock Factor-1 Recruitment and Gene Expression of CXC Chemokine Genes," Cytokine, Author manuscript, available in PMC, 2012, 14 pages.

Mas, Valeria et al., "Gene Expression Patterns in Deceased Donor Kidneys Developing Delayed Graft Function After Kidney Transplantation," Transplantation, vol. 85, No. 4, 2008, 10 pages.

Mazanowska, O. et al, "Imbalance of Metallaproteinase/Tissue Inhibitors of Metalloproteinase System in Renal Transplant Recipients With Chronic Allograft Injury." Transplantation Proceedings, vol. 43, 2011, 4 pages.

Messina, G., et al., "Microfluidic immunosensor design for the quantification of interleukin-6 in human serum samples," Analytical Biochemistry, vol. 380, 2008, 6 pages.

Metters, J. et al., "New directions in screen printed elctroanalytical sensors: an overview of recent developments," Analyst, vol. 136, 2011, 10 pages.

Musial K., et al., "Heat shock proteins in chronic kidney disease," Journal of the International Pediatric Nephrology Association, 2010, 9 pages.

Nakaya, R. et al., "Identification of proteins that may directly interact with human RPA," J. Biochem, vol. 148, No. 5, 2010, 9 pages.

Nath, N. et al., "Evanescent wave fibre optic sensor for detection of L. donovani specific antibodies in sera of kala azar patients," Biosensors & Bioelectronics, 1996, 8 pages.

Obeidat, Motaz A., et al., "Post-transplant nuclear renal scans correlate with renal injury; biomarkers and early allograft outcomes," Nephrol Dial Transplant, vol. 26, 2011, 8 pages.

Orellana G. et al., "New Trends in Fiber-Optic Chemical and Biological Sensors," Current Analytical Chemistry, vol. 4, 2008, 23 pages.

Pache, G. et al., "Upregulation of Id-1 via BMP-2 receptors induces reactive oxygen species in podocytes," Am J Physiol Renal Physiol, vol. 291, 2006, 9 pages.

Panini, N. et al., "Intergrated microfluidic systems with an immunosensor modified with carbon nanotubes for detection of prostate specific antigen (PSA) in human serum samples," Biosensors and Bioelectronics, vol. 23, 2008, 7 pages.

Paulis, L. et al., "Novel therapeutic targets for hypertension," Nature Reviews: Cardiology, vol. 7, 2010, 11 pages.

Pereira, Rui et al., "Neutrophil and rnonocyte activation in chronic kidney disease patients under hemodialysis and its relationship with; resistance to recombinant human erythropoietin and to the hemodialysis procedure," Hemodialysis International. vol. 14, 2010, 7 pages.

Ransom, Richard F. et al., "Differential proteomic analysis of proteins induced by gluecocorticoids in cultured murine podocytes," Kidney International, vol. 67, 2005, 1275-1285.

Reich, Heather N. et al., "Molecular Markers of Injury in Kidney Biopsy Specimens of Patients with Lupus Nephritis," The Journal of Molecular Diagnostics, vol. 13, No. 2, 2011, 9 pages.

Romanenko, Alina et al., "p16INK4A and p15INK4B Gene Alteration Associated; with Oxidative Stress in Renal Cell Carcinomas; After the Chernobyl Accident (Pilot Study)," Diagnostic Molecular Pathology,vol. 11, No. 3, 2002, 163-169.

Ruotsalainen, V. et al., "Nephrin is specifically located at the slit diaphragm of glomerular podocytes," Proc. Natl. Acad. Sci. USA, vol. 96, 1999, 6 pages.

Rusling, J. et al., "Measurement of biomarker proteins for point-of-care early detection and monitoring of cancer," Analyst, Author manuscript, available in PMC, 2010, 31 pages.

Rusnati, M. et al., "Exploiting Surface Plasmon Resonance (SPR) Technology for the Identification of Fibroblast Growth Factor-2 (FGF2) Antagonists Endowed with Antiangiogenic Activity," Sensors, vol. 9, 2009, 33 pages.

Sadik, O. et al., "Status of biomolecular recognition using electrochemical techniques," Biosensors and Bioelectronics, vol. 24, 2009, 17 pages.

Saito, S. et al., "Analysis of glial cell line-derived neurotrophic factor-inducible zinc finger protein 1 expression in human diseased kidney," Human Pathology, col. 42, 2011, 11 pages.

Sataranatarajan, K. et al., "Regulation of Elongation Phase of mRNA Translation in Diabetic Nephropathy," The American Journal of Pathology, vol. 171, No. 6, 2007, 10 pages.

Sigdel, Tara K. et al., "Shotgun Proteomics Identifies Proteins Specific for Acute Renal; Transplant Rejection," Proteomics Clin Appl. Author manuscript; available in PMC 2010, 27 pages.

Snigdha, Shikha et al., "Caspase-3 activation as a bifurcation point between plasticity and cell; death," Neurosci Bull, vol. 28, No. 1, 2012, 11 pages.

Soleimani, M., "Dietary fructose, salt absorption and hypertension in; metabolic syndrome: towards a new paradigm," Acta Physiol, vol. 201, 2011, 55-62.

Sonna, L. et al., "Molecular Biology of Thermoregulation Invited Review: Effects of heat and cold stress on mammalian gene expression," J Appl Physiol, vol. 92, No. 1725, 2002, 17-42.

Struckmann, Kirsten et al., "Impaired Expression of the Cell Cycle Regulator BTG2 Is Common in Clear Cell Renal Cell Carcinoma," Cancer Res, vol. 64, 2004, 1632-1638.

Su, Y. et al., "Chromatic immunoassay based on polydiacetylene vesicles," Colloids and Surfaces B: Biointerfaces, vol. 38, 2004, 5 pages.

Sun, A. et al., "Sensitive label-free electrochemical immunoassay based on a redox matrix of gold nanoparticles/Azure I/multi-wall carbon nanotubes composite," Biochemical Engineering Journal, vol. 57, 2011, 6 pages.

Sun, Dong et al., "Thrombospondin-1 Short Hairpin RNA Suppresses Tubulointerstitial Fibrosis in the Kidney of Ureteral Obstruction by Ameliorating Peritubular Capillary Injury," Kidney Blood Press Res, vol. 35, 2012, 6 pages.

Tiniakos, D. et al, "Ontogeny of intrinsic innervation in the human kidney," Anal Embryol, vol. 209, 2004, 7 pages.

Todorov, Vladimir et al., "Differential Regulation of Cathepsin B and Prorenin Gene Expression in Renal Juxtaglomerular Cells," Kidney Blood Press Res, vol. 24, 2001, 4 pages.

Trimarchi, Hernan et al., "Proteinuria: an ignored marker of inflammation and cardiovascular disease in chronic hemodialysis," International Journal of Nephrology and Renovascular Disease, vol. 5, 2012, 7 pages.

Vivekanandan, A. et al., "Urine Glycoprotein Profile Reveals Novel Markers for Chronic Kidney Disease," International Journal of Proteomics, 2011, 18 pages.

Waalkes et al., "Fibronectin 1 mRNA expression correlates with advanced disease in renal cancer," Cancer, vol. 10, 2010, 6 pages.

Wang, Bao-Ying et al., Hepatotoxicity and gene expression downregulation of CYP isozymes caused by renal ischemia/reperfusion in the rat, Experimental and Toxicologic Pathology 61 (2009) 169-176.

Wong, Dona L. et al., "Adrenergic Responses to Stress: Transcriptional and Post-Transcriptional Changes," Ann N Y Acad Sci. Author manuscript; available in PMC, 2009, 10 pages.

Wu, Huiling et al., "TLR4 activation mediates kidney ischemia/reperfusion injury," The Journal of Clinical Investigation, vol. 117, No. 10, 2007, 2847-2859.

Xie, Chaogin, "Ablation of Transient Receptor Potential Vanilloid 1 Abolishes Endothelin-Induced Increases in Afferent Renal Nerve Activity: Mechanisms and Functional Significance," Hypertension, vol. 54, 2009, 1298-1305.

(56) References Cited

OTHER PUBLICATIONS

Xie, Chaoqin, Interdependent Regulation of Afferent Renal Nerve Activity and Renal Function: Role of Transient Receptor Potential Vanilloid Type 1, Neurokinin 1, and Calcitonin Gene-Related Peptide Receptors, The Journal of Pharmacology and Experimental Therapeutics, vol. 325, No. 3, 7 pages.

Yoshino, Jun et al., "Leukemia Inhibitory Factor Is Involved in Tubular Regeneration after Experimental Acute Renal Failure," J Am Soc Nephrol, vol. 14, 2003, 3090-3101.

Yuan, B. et al., "Gene expression reveals vulnerability to oxidative stress and interstitial fibrosis of renal outer medulla to nonhypertensive elevations of ANG II," Am J. Physiol Regul Integr Comp Physiol, vol. 284, 2003, 12 pages.

Zager, Richard et al., "Acute unilateral ischemic renal injury induces progressive renal inflammation, lipid accumulation, histone modification, and "end-stage" kidney disease," Am J Physiol Renal Physiol, vol. 301, 2011, 12 pages.

Zeisberg, Michael, "Bone morphogenic protein-7 and the kidney: current; concepts and open questions," Nephrol Dial Transplant, vol. 21, 2006, 6 pages.

Zerega, Barbara et al., "Expression of NRL/NGAL (neu-related lipocalin/neutrophil gelatinase-associated lipocalin) during mammalian embryonic development and in Inflammation." European Journal of Cell Biology, vol. 79, 2000 8 pages.

Zhang, Weiru et al. "Interleukin 6 Underlies Angiotensin II-Induced Hypertension and Chronic Renal Damage," Hypertension, vol. 59, 2012, 136-144.

Zhao, Hongcheng et al., "Activation of the Transcription Factor Oct-1 in Response to DNA Damage," Cancer Res, vol. 60, 2000, 6 pages.

Staal, S.S., et al., "A Prefilled, ; Ready-to-Use, Electrophoresis-Based ; Lab-on-a-Chip Device for Monitoring Ions in ; Blood and Urine." 14th International ; Conference on Miniaturized Systems for ; Chemistry and Life Sciences, Oct. 3-7, 2010, Groningen, The Netherlands. 3 pages.

Rusling, James F., "Nanomaterials-; Based Electrochemical Immunosensors; for Proteins." The Chemical Record, 12 (1), Feb. 2012. 13 pages.

Yanase, Yuhki; et al., "Development of an; Optical Fiber SPR Sensor for Living Cell; Activation." Biosensors and Bioelectronics, 25 (5), Jan. 15, 2010. 16 pages.

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical investigation, vol. 56, Jul. 1975, pp. 208-217.

Bello-Reuss, E. et al.,, "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Fain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J, Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephroi Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation onthe Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

Schlaich, M.P. et al., "Renal Denervation as a Therapeutic Approach for Hypertension: Novel Implications for an Old Concept," Hypertension, 2009; 54:1195-1201.

Schlaich, M.P. et al., "Renal Sympathetic-Nerve Ablation for Uncontrolled Hype nsion," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16: 1 page.

Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter,"Journal of the American College of Cardiology, 1999; 33; pp. 972-984.

Beale et al., "Minimally Invasive Treatment for Varicose Veins: A Review of Endovenous Laser Treatment and Radiofrequency Ablation", Lower Extremity Wounds 3(4), 2004, 10 pages.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

(56) References Cited

OTHER PUBLICATIONS

Clinica Trials.gov, Renal Denervation in Patients with uncontrolled Hypertension in Chinese (2011), 6pages. www.clinicaltrials.gov/ct2/show/NCT01390831.

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.

Exceprt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. 2465470, Granted Oct. 28, 2015, Date of Opposition Jul. 27, 2016, 34 pp.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Opposition to European Patent No. EP2092957, Granted Jan. 5, 2011, Date of Opposition Oct. 5, 2011, 26 pages.

Oz, Mehmet, Pressure Relief, Time, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Pieper, et al., "Design and Implementation of a New Computerized System for Intraoperative Cardiac Mapping" Journal of Applied Physiology, 1991, vol. 71 (4), pp. 1529-1539.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20:484-490, 2005.

Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.

Schneider, Peter A., "Endovascular Skills—Guidewire and Catheter Skills for Endovascular Surgery," Second Edition Revised and Expanded, 10 pages, (2003).

ThermoCool Irrigated Catheter and Integrated Ablation System, Biosense Webster (2006), 6 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

U.S. Appl. No. 11/363,867, filed Feb. 27, 2006, 70 pp.

U.S. Appl. No. 60/813,589, filed Dec. 29, 2005, 62 pgs.

U.S. Appl. No. 60/852,787, filed Oct. 18, 2006, 112 pgs.

Ureter, https://en.wikipedia.org/wiki/Ureter, Jun. 2016, 6 pgs.

Wittkampf et al., "Control of radiofrequency lesion size by power regulation," Journal of he American Heart Associate, 1989, 80: pp. 962-968.

Zheng et al., "Comparison of the temperature profile and pathological effect at unipolar, bipolar and phased radiofrequency current configurations," Journal of interventional Cardiac Electrophysiology, 2001, pp. 401-410.

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatrnent-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=iroi-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.

"Iberis—Renal Sympathetic Denervation System: Turning innovation into quality care." [Brochure], Terumo Europe N.V., 2013, Europe, 3 pages.

"Neurotech Reports Announces Wnners of Gold Electrode Awards." Neurotech business report, 2009. 1 page. <http://www.neurotechreports.com/pages/goldelectrcodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical intelligence: A blog specializing in Pharmaceutical Intelligence and Analytics, Nov. 8, 2012, 21 pages, <http://pharmaceuticalintelligence.com/tag/vessix-vascular/>.

"The Edison AwardsTM" Edison Awards: Honoring Innovations & Innovators, 2013, 2 pages, <http://www.edisonawards.com/Awards.php>.

"The Future of Renal denervation for the Treatment of Resistant Hypertension," St. Jude Medical, Inc., 2012, 12 pages.

"Vessix Renal Denervation System: So Advanced It's Simple," [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 199,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

(56) References Cited

OTHER PUBLICATIONS

Brosky, John, "EuroFCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Curtis, J.J., et al., "Surgical therapy for persistent hypertension after renal transplantation." Transplantation, 1981, 31: 125-128.
Davis, Mark et al., "Effectiveness of Renal Denervation Therapy for Resistant Hypertension." Journal of the American College of Cardiology, vol. 62; No. 3, 2013, 11 pages.
Stouffer. G. A. et al., "Catheter-based renal denervation in the treatment of resistant hypertension." Journal of Molecular and Cellular Cardiology; vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for he Control of Hypertension, ICI 2012, Dec. 5-6, 2012. 38 pages.
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Doumas, Michael et al., "Renal Nerve Ablation for Resistant Hypertension: The Dust Has Not Yet Settled." The Journal of Clinical Hypertension. 2014; vol. 16, No. 6, 2 pages.
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of Renal failure and Hypertension." U.S. Appl. No. 60/442,970, filed Jan. 29, 2003, 23 pages.
Gertner, Jon, "Meet The Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
International Search Report and Written Opinion, International Application No. PCT/US2015/047568, dated Dec. 15, 2015, 10 pages.
Linz, Dominik et al,, "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias," Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Messerli, Franz H. et al. "Renal Denervation for Resistant Hypertension: Dead or Alive?" Healio: Cardiology today's Intervention, May/Jun. 2014, 2 pages.
Millard, F. C., et al, "Renal Embolization for ablation of function in renal failure and hypertension." Postgraduate Medical Journal, 65, 729-734, (1989).
Miller, Reed, "Finding a Future for Renal Denervation With Better Controlled Trials." Pharma & Medtech Business Intelligence, Article # 01141006003, Oct. 6, 2014, 4 pages.
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally ppublished online Dec. 11, 2006).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

(56) References Cited

OTHER PUBLICATIONS

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter Ablation of Cardiac Autonomic Nerves for Prevention of Vagal Atrial Fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et. al,, "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Smithwick et al., "Splanchnicectomy for essential hypertension." J. Am. Med. Assn. 152:16 (1953), pp. 1501-1504.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversable renal denervation on haemodynamic and excretory functions on the ipsilateral and contralateral kidney in the cat." Hypertension, 4: 181-188 (1986).

* cited by examiner

METHODS FOR ASSESSING EFFICACY OF RENAL NEUROMODULATION AND ASSOCIATED SYSTEMS AND DEVICES

CROSS-REFERENCE TO RELATED APPLICATION(S)

This application is a U.S. National Phase under 35 U.S.C. 37 of International Application No. PCT/US15/47568 files Aug. 28, 2015, which claims the benefit of U.S. Provisional Patent Application No. 62/042,281, filed Aug. 28, 2014, and incorporated herein by reference in their entireties.

ADDITIONAL APPLICATION(S) INCORPORATED BY REFERENCE

The following application is incorporated herein by reference in its entirety:

International PCT Patent Application No. PCT/US2013/030041, entitled "BIOMARKER SAMPLING IN THE CONTEXT OF NEUROMODULATION DEVICES AND ASSOCIATED SYSTEMS," filed Mar. 8, 2013.

As such, components and features of embodiments disclosed in this application may be combined with various components and features disclosed in the present application.

TECHNICAL FIELD

The present technology is related to neuromodulation, such as renal neuromodulation and systems, devices, and methods for assessing efficacy of renal neuromodulation on subjects.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via radio frequency (RF) ablation) have been shown to reduce blood pressure in patients with treatment-resistant hypertension.

BRIEF DESCRIPTION OF DRAWINGS

Many aspects of the present disclosure can be better understood with reference to the following drawing(s). The components in the drawings are not necessarily to scale. Instead, emphasis is placed on illustrating clearly the principles of the present disclosure.

DETAILED DESCRIPTION

Figure 1:
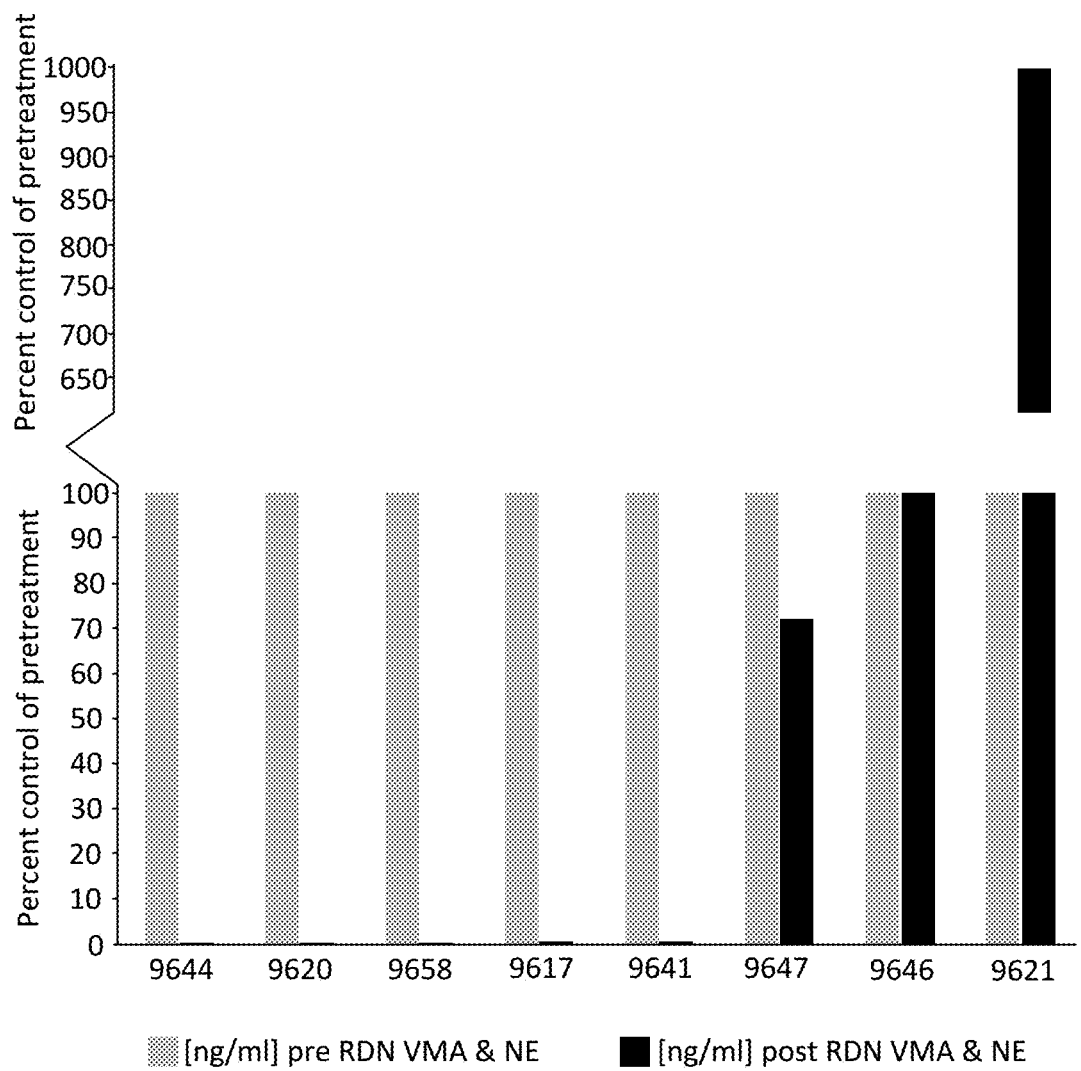
FIG. 1 is a plot of vanillylmandelic acid and noradrenaline concentration levels in urine collected before and after renal neuromodulation procedures performed in animal subjects.

The present technology is directed to methods, systems, devices and compositions for monitoring, assessing and/or determining neuromodulation efficacy by detecting changes in the level of one or more surrogate biomarkers (e.g., associated with hypertension, high blood pressure, norepinephrine spillover, etc.) in plasma or urine in a patient. Specific details of several embodiments of the technology are described below with reference to FIGS. 1-3. Although many of the embodiments are described below with respect to methods, systems, devices and compositions for monitoring and/or determination of renal neuromodulation efficacy, other applications (e.g., monitoring levels of surrogate biomarkers in the absence of neuromodulation) and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-3.

Several current methods for neuromodulation would benefit from a process for relatively non-invasive and rapid evaluation of success of the procedure. Examples of neuromodulation methods that may benefit from non-invasive, rapid evaluation and/or efficacy assessment methods include renal denervation, for example to treat clinical conditions characterized by increased overall sympathetic activity and, particularly, renal sympathetic activity. Such clinical conditions can include hypertension, metabolic syndrome, insulin resistance, diabetes, left ventricular hypertrophy, chronic end stage renal disease, inappropriate fluid retention in heart failure, cardio-renal syndrome, osteoporosis, and sudden death.

"Neuromodulation" is the partial or complete incapacitation or effective disruption of one or more nerves. Such incapacitation or disruption can be long term (e.g., permanent or for periods of months or years) or short term (e.g., for periods of minutes, hours, days, or weeks). "Renal neuromodulation" is the partial or complete incapacitation or effective disruption of the nerves of the kidneys, including nerves terminating in the kidneys or in structures closely associated with the kidneys. Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death, among others. The reduction of afferent neural signals typically contributes to the systemic reduction of sympathetic tone/drive, and renal neuromodulation is expected to be useful in treating several conditions associated with systemic sympathetic overactivity or hyperactivity.

In one example, spillover (e.g., renal or total body) plasma norepinephrine levels is a marker of elevated sympathetic nerve activity. Accordingly, a decrease in sympathetic nerve activity may be observed via a marker of sympathetic nerve activity in patients having hypertension, such as decreased levels of plasma norepinephrine (noradrenaline).

Biomolecules, such as catecholamines and other neuropeptides, are known to be involved in the modulation of blood pressure. As an example, radiotracer dilution has demonstrated increased renal NE spillover rates in patients with essential hypertension. At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, NE binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands. As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of NE from the kidneys to plasma revealed increased renal NE spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced SNS overactivity.

Both chronic and end-stage renal disease are characterized by heightened sympathetic nerve activation. In patients with end-stage renal disease, plasma levels of NE above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic overactivity, such as hypertension, left ventricular hypertrophy, ventricular arrhythmias, sudden cardiac death, insulin resistance, diabetes, and metabolic syndrome.

In accordance with aspects of the present technology, a decrease in sympathetic nerve activity may be observed via a marker of sympathetic nerve activity in patients having hypertension, such as decreased levels of plasma NE (noradrenaline), changes in levels of systemic renin in plasma, and/or changes in levels of systemic aldosterone in plasma. Other measures or markers of sympathetic nerve activity can include muscle sympathetic nerve activity (MSNA), NE spillover, and/or heart rate variability. Other measurable physiological parameters or markers, such as improved blood pressure control, changes in aldosterone-to-renin ratio (ARR), changes in a salt suppression test, changes in blood plasma levels of potassium, etc., can also be used to assess efficacy of the renal neuromodulation treatment for patients having hypertension. In certain embodiments, renal neuromodulation may be repeated one or more times at various intervals until a desired sympathetic nerve activity level or another therapeutic benchmark is reached.

In some embodiments, renal neuromodulation is expected to result in a change in blood pressure and/or sympathetic nerve activity over a specific timeframe. For example, in certain of these embodiments, blood pressure and/or sympathetic nerve activity levels are decreased over an extended timeframe, e.g., within 1 month, 2 months, 3 months, 6 months, 9 months or 12 months post-neuromodulation.

Efficacy of many current renal neuromodulation methods is evaluated after the procedure has been completed by monitoring acute changes in blood pressure, but statistically meaningful changes in blood pressure may not be observed until about 2 weeks, 4 weeks, 3 months, 6 months, or more after completion. Moreover, blood pressure changes can be inherently variable in individual patients due to time, activity level, adrenal fatigue, long-term or short-term pharmacological intervention and a host of other factors. In the absence of relatively contemporaneous feedback (e.g., less than about 30 minutes) and/or additional, less variable biochemical reporting of renal neuromodulation efficacy, interventionists may not have a reliable assessment of the immediate efficacy of the treatment procedure, the long-term clinical outcome of the patient due to the procedure, and/or the value of a repeat procedure to meet therapeutic benchmarks in individual patients.

I. METHODS FOR ASSESSING EFFICACY OF RENAL NEUROMODULATION

Disclosed herein are several embodiments of methods and processes for monitoring and assessing neuromodulation efficacy by detecting changes in the level of one or more surrogate biomarkers associated with hypertension and/or high blood pressure, as well as methods and processes of performing neuromodulation that incorporate monitoring or determination of neuromodulation efficacy based on changes in level of one or more surrogate biomarkers. The disclosed methods are expected to allow for procedure-specific, non-invasive and/or relatively contemporaneous monitoring of neuromodulation efficacy. In certain embodiments, these methods and processes are used to monitor the efficacy of renal neuromodulation. Also provided herein are methods of treating hypertension in a subject in need thereof using renal neuromodulation, wherein the methods include steps for monitoring and/or assessing the efficacy of the neuromodulation procedure by detecting changes in the level of one or more surrogate biomarkers associated with hypertension and/or high blood pressure. Further provided herein are devices and compositions for use in conjunction with the disclosed methods.

Several embodiments of methods for monitoring neuromodulation efficacy by detecting changes in the level of one or more surrogate biomarkers in accordance with the present technology are described herein. As used herein "surrogate biomarker" can refer to a biomarker that directly or indirectly correlates with sympathetic nervous activity in the patient, or in another embodiment, a biomarker that directly or indirectly correlates with blood pressure. In certain embodiments, these methods can be used to determine whether a neuromodulation procedure was successful (e.g., whether the procedure resulted in partial or complete incapacitation or effective disruption of one or more target nerves and achieved a desirable therapeutic response), partially successful (e.g., whether the procedure resulted in incomplete or partial disruption of one or more target nerves and achieved a partially desirable therapeutic response), or was unsuccessful (e.g., whether the procedure resulted in incomplete disruption or no disruption of one or more target nerves and did not achieve a desirable therapeutic response).

Surrogate biomarker(s) for use in conjunction with the methods disclosed herein may be any biomolecule that exhibits a quantitative and detectable change in level following neuromodulation in a desired manner. In certain embodiments, for example, surrogate biomarkers may be proteins or metabolites thereof. In these embodiments, a change in protein level may refer to a change in expression (as measured by mRNA or protein level) or secretion. In other embodiments, surrogate biomarkers may be small molecules, peptides, or other non-protein compounds. Provided in certain embodiments are compositions comprising one or more surrogate biomarkers and/or one or more reagents or detection agents for use in detection and/or quantification of the biomarker(s) and for use in the methods disclosed herein.

In particular embodiments, the surrogate biomarkers may be small molecules such as catecholamines or other neurotransmitters (particularly those associated with sympathetic nervous activity) such as NE, epinephrine, dopamine or secreted metabolites or cellular debris thereof. Catecholamines (NE, epinephrine, dopamine) break down into other biomolecules (e.g., metabolites), which leave the body through urine excretion. For example, NE breaks down into metabolites normetanephrine and vanillylmandelic acid (VMA); epinephrine breaks down into metabolites metanephrine and VMA; and dopamine breaks down into metabolite homovanillic acid (HVA). Accordingly, in one embodiment, changes in concentration levels of particular catecholamines in plasma, or in other embodiments, concentration levels of particular catecholamines and metabolites of catecholamines (or combinations thereof) in urine can be determined and compared (a) between pre- and post-neuromodulation treatment, and/or (b) between post-neuromodulation treatment and pre-determined range of concentration level(s).

In other embodiments, the surrogate biomarkers may be neuropeptides, such as neuropeptide Y (NPY) and vasopressin, which are implicated systemic markers of hypertension. NPY is a neuropeptide that acts as a neurotransmitter in the brain and in the autonomic nervous systems of humans and is known to function as a vasoconstrictor. The NPY gene is widely expressed in the peripheral and central nervous systems and is involved in diverse physiological functions including blood pressure regulation. Plasma NPY levels correlate with blood pressure levels and have been shown to be elevated in hypertensive patients (*Hypertension*. November 2012; 60(5): 10.1161/HYPERTENSIONAHA.112.197855). Vasopressin is a neurohypophysial hormone that functions to retain water in the body (e.g., by increasing water reabsorption in the collecting ducts of the kidney nephron) and to increase peripheral vascular resistance (e.g., by inducing vasoconstriction), which in turn increases arterial blood pressure. Vasopressin has been implicated as being expressed highly in the plasma as a result of hypertension (Changes Of Vasopressin In Hypertension: Cause Or Effect? *The Lancet*, Volume 307, Issue 7972, Pages 1255-1257). Accordingly, in one embodiment, changes in concentration levels of NPY or Vasopressin in plasma can be determined and compared (a) between pre- and post-neuromodulation treatment, and/or (b) between post-neuromodulation treatment and pre-determined range of concentration level(s).

In additional embodiments, the surrogate biomarkers may be proteins, such as globular proteins found in urine and plasma. For example, the surrogate biomarker can be albumin, or microalbuminuria detected in urine. Albumin levels in the urine can be used to show early indication of deteriorating renal function and increased vascular permeability. It is known that patients with high blood pressure levels have increased levels of albumin or microalbuminuria excreted from the patient in urine. Accordingly, in one embodiment, changes in concentration levels of albumin or microalbuminuria in plasma and/or urine can be determined and compared (a) between pre- and post-neuromodulation treatment, and/or (b) between post-neuromodulation treatment and pre-determined range of concentration level(s).

In further embodiments, the surrogate biomarkers may be biomolecules that participate in the body's renin-angiotensin aldosterone system (RAAS), which regulates blood pressure and water (fluid) balance. For example, the components of RAAS, can, in part, regulate a body's mean arterial blood pressure, such as by mediating extracellular volume (e.g., blood plasma, lymph, interstitial fluid), and arterial vasoconstriction. Renin, which is an angiotensinogenase, is secreted by the afferent arterioles of the kidney from specialized cells of the juxtaglomerular apparatus and in response to decreases in arterial blood pressure or sodium levels and sympathetic nervous system activity. Renin primarily activates other components of the RAAS, which ultimately results in an increase in arterial blood pressure. The adrenal glands produce aldosterone as part of the RAAS, which causes the tubules of the kidneys to increase the reabsorption of ions (e.g., sodium) and water into the blood, which, in turn, increases blood volume and blood pressure.

Renal sympathetic activity causes the kidneys to increase renin production, which ultimately leads to increased aldosterone production via the RAAS. Elevated renin production and increased aldosterone levels in plasma are correlated with elevated renal sympathetic activity and hypertension. Accordingly, these neural regulation components of renal function are considerably stimulated in disease states characterized by heightened sympathetic tone and likely contribute to increased blood pressure in hypertensive patients. Renal neuromodulation is expected to reduce renal sympathetic neural activity, thereby causing a reduction in elevated renin production, and decreased aldosterone production. Intravascular devices that reduce sympathetic nerve activity by applying, for example, RF energy to target site(s) along the renal artery have recently been shown to reduce blood pressure in patients with treatment-resistant hypertension. Accordingly, in one embodiment, changes in concentration levels of renin, aldosterone or other components of RAAS in plasma and/or urine can be determined and compared (a) between pre- and post-neuromodulation treatment, and/or (b) between post-neuromodulation treatment and pre-determined range of concentration level(s).

In certain embodiments, the methods disclosed herein can include (a) determining a baseline level of one or more surrogate biomarkers in plasma and/or urine; (b) performing the neuromodulation procedure; (c) determining a post-neuromodulation level for the surrogate biomarker(s) in plasma and/or urine; and (d) comparing the post-neuromodulation level to the baseline level, wherein the neuromodulation procedure is classified as at least partially successful if the post-neuromodulation level differs significantly from the baseline level. In certain embodiments, a significant difference in level means a difference of about 10% or greater, about 20% or greater, about 30% or greater, about 40% or greater, about 50% or greater, about 60% or greater, about 70% or greater, about 80% or greater or about 90% or greater. In other embodiments, a significant difference in level means a difference of about 2-fold or greater, for example about 3-fold or greater, about 4-fold or greater, or about 5-fold or greater. For some biomarkers, the post-neuromodulation level is expected to be significantly less (e.g., reduced) than the baseline level. For other biomarkers, the post-neuromodulation level is expected to be significantly greater (e.g., increased) than the baseline level.

In other embodiments, these methods can include (a) performing the neuromodulation procedure; (b) determining a post-neuromodulation level for one or more surrogate biomarkers in plasma and/or urine; and (c) comparing the post-neuromodulation level to a pre-determined threshold level, wherein the neuromodulation procedure is classified as at least partially successful if the post-neuromodulation level is less than the pre-determined threshold level. In another embodiment, the neuromodulation procedure can be classified as at least partially successful if the post-neuromodulation level is no greater than about 5%, or about 10%, or about 20% above the pre-determined threshold level. In one embodiment, the pre-determined threshold level can be an upper limit of a normal range of level for the biomarker(s). In other embodiments, the pre-determined threshold level can be a different value (e.g., an average level achieved for patients having undergone successful or partially successful renal neuromodulation).

In still other embodiments, these methods include (a) performing the neuromodulation procedure; (b) determining a post-neuromodulation level for one or more surrogate biomarkers in plasma and/or urine; and (c) comparing the post-neuromodulation level to a pre-determined range of level, wherein the neuromodulation procedure is classified as successful if the post-neuromodulation level falls within or near the pre-determined range of level. In particular examples of assessing neuromodulation efficacy via changes in concentration levels of catecholamines and metabolites thereof, patient urine can be collected over a 24 hour period following neuromodulation treatment in the patient. The pre-determined range of concentration levels can be normal values found in human urine (collected and assessed over a 24 hour period). Patient urine can be examined for levels of individual catecholamines and their metabolites and can be compared to the normal values. Table 1 below sets forth normal values of catecholamines and metabolites of catecholamines found in urine over a 24 hour period of time.

TABLE 1

Normal Concentration of Catecholamines and Metabolites in Human Urine

| Biomolecule | Concentration/24 hours |
| --- | --- |
| Dopamine | 65-400 mcg/24 hours |
| Epinephrine | 0.5-20 mcg/24 hours |
| Metanephrine | 24-96 mcg/24 hours* |
| Norepinephrine | 15-80 mcg/24 hours |
| Normetanephrine | 75-375 mcg/24 hours |
| Vanillylmandelic acid | 2-7 mg/24 hours |
| Total urine catecholamines | 14-110 mcg/24 hours |

*Some laboratories report the normal range as 140-785 mcg/24-hours.

In certain embodiments, a post-neuromodulation surrogate biomarker level is determined in an acute timeframe (e.g., within about 15 minutes following denervation, within 30 minutes or less following denervation, etc.). In some embodiments, neuromodulation efficacy by determining a surrogate biomarker level in plasma or urine can be assessed while a subject is still catheterized (e.g., within the renal vasculature). In other embodiments, however, post-neuromodulation biomarker level may be measured in a chronic timeframe, e.g., within several hours, days, weeks, or months following denervation. For example, the post-neuromodulation biomarker level can be determined at about 15 minutes, about 24 hours and/or about 7 days post-denervation. In another example, the post-neuromodulation biomarker level can also be determined about 1 month, about 3 months and/or about 6 months post-denervation. In certain embodiments, the methods provided herein include (a) determining a baseline level of one or more surrogate biomarkers in plasma and/or urine collected from a patient, (b) at least partially inhibiting sympathetic neural activity in a renal nerve of the subject via a neuromodulation assembly (discussed in more detail below), (c) determining a post-neuromodulation level for the surrogate biomarker(s) in plasma and/or urine collected from the patient, and (d) comparing the post-neuromodulation level to the baseline level, wherein the neuromodulation procedure is classified as at least partially successful if the post-neuromodulation level differs significantly from the baseline level.

The surrogate biomarkers presented herein may have their own unique physiological response profile following a successful or sufficient neuromodulation procedure. In some examples, a surrogate biomarker is expected to demonstrate a decrease in level compared to a baseline, threshold or other predetermined level in an acute time-frame, in a chronic time-frame, or both. In other examples, a surrogate biomarker is expected to demonstrate an increase in level compared to a baseline, threshold or other predetermined level in the acute time-frame, chronic time-frame, or both. In still other examples, certain surrogate biomarkers may demonstrate other physiological response profiles that include both increases and decreases as either concentration spikes/dips or slower trends over time. In a particular example, such a surrogate biomarker may show a significant increase (e.g., a concentration spike) in an acute time frame followed by a significant lowering over time (e.g., chronic time-frame) as a result of a successful neuromodulation treatment. Accordingly, surrogate biomarkers can be selected, in part, based on their unique physiological response profile, a patient's baseline profile, or other factors for assessing renal neuromodulation efficacy post-treatment.

Also described herein are several embodiments of methods for determining surrogate biomarker levels in a patient in accordance with the present technology. In certain of these embodiments, these methods include (a) collecting a first plasma and/or first urine sample from a patient, (b) determining a first concentration of one or more surrogate biomarker(s) via enzyme immunoassay, (c) transluminally positioning an energy delivery element of a catheter within a target blood vessel of the patient and adjacent to target neural fibers, (d) at least partially ablating the target neural fibers via the energy delivery element, (e) collecting a second plasma and/or second urine sample from the patient, (f) determining a concentration of one or more surrogate biomarker(s) via enzyme immunoassay, and (g) comparing the first concentration to the second concentration, wherein, the difference between the first concentration and the second concentration corresponds, at least in part, to a degree of ablation of the target renal neural fibers.

In certain embodiments of the methods disclosed herein, where neuromodulation is carried out at or near the kidney (e.g., in the renal artery), changes in surrogate biomarker level may be measured in a systemic biological sample obtained from the patient, for example by collecting a blood or urine sample. A "biological sample" as used herein may refer to any bodily fluid (e.g., blood, plasma, urine, etc.) or tissue that may contain one or more surrogate biomarkers. In various embodiment disclosed herein, the level of a biomarker can be determined from a biological sample obtained from the bladder (e.g., urine). In one embodiment, the urine sample may be collected via urethral catheterization. In another embodiment, the urine sample may be collected by the patient in a cup or vial during normal urine excretion. Additional embodiments disclosed herein include assessing a level of a biomarker from a patient plasma sample. Plasma samples, for example, may be prepared from routine blood samples collected via conventional techniques used by biological and clinical laboratory technicians.

Surrogate biomarkers for use in the methods disclosed herein may exhibit a change in level that correlates with nerve ablation and/or whole body NE levels. In certain embodiments, for example, changes in the level of a surrogate biomarker may be a direct result of neuromodulation, e.g., a direct response to neuronal damage. Changes in the level of a surrogate biomarker may be indicative of a synaptic discharge of substances such as small molecules (e.g., calcium) or neurotransmitters as a result of axonal damage, axonal stress, or axotectomy. For example, sympathetic denervation might result in discharge of NE, NPY, or dopamine reserves at the synaptic ends in the kidney, resulting in a burst and/or subsequent decline that can be collected and detected from renal arterial or venous blood or elsewhere such as in systemic blood or urine. In other embodiments, changes in the level of a biomarker may be an indirect/surrogate response to the neuromodulation procedure. For example, a surrogate biomarker may be a metabolite or other product of catabolism of catecholamines (e.g., NE, epinephrine, etc.) that is excreted in urine.

In certain embodiments of the methods disclosed herein, neuromodulation efficacy is monitored and/or assessed by detecting changes in the level of a single surrogate biomarker. In other embodiments, efficacy is monitored and/or assessed by detecting changes in the level of two or more surrogate biomarkers. In certain of these embodiments, neuromodulation is classified as successful or at least partially successful if each of the surrogate biomarkers exhibits a change in level. In other embodiments, neuromodulation is classified as successful if a threshold number or a specific subset or combination of surrogate biomarkers exhibits a change in level. In those embodiments that utilize two or more surrogate biomarkers, the surrogate biomarkers may be all proteins, all non-proteins, or a combination of proteins and non-proteins. For example, the surrogate biomarkers maybe catecholamines and/or metabolites thereof, neuropeptides and/or combinations thereof.

In certain embodiments of the methods disclosed herein, baseline level of a surrogate biomarker is derived from the subject undergoing neuromodulation. For example, surrogate biomarker level may be measured in the subject at one or more timepoints before neuromodulation. The baseline value may represent a surrogate biomarker level at a specific timepoint before neuromodulation, or it may represent an average level at two or more timepoints before neuromodulation. In certain embodiments, a baseline value is based on surrogate biomarker level immediately before neuromodulation (i.e., after the subject has already been catheterized for renal neuromodulation). Alternatively, a baseline value for a particular surrogate biomarker may be derived from a standard value for that surrogate biomarker across the population as a whole or across a particular subpopulation. In certain embodiments, the baseline level of a surrogate biomarker is determined using the same method that is subsequently used to determine the post-neuromodulation level of the surrogate biomarker. In certain embodiments, changes in surrogate biomarker level are calculated based on the difference between baseline level and post-neuromodulation level. For example, the differential (delta) in surrogate biomarker concentration levels can be the difference between surrogate biomarker concentration levels at a specific timepoint pre- and post-neuromodulation.

Surrogate biomarkers for use in the methods disclosed herein may exhibit a two-fold or greater change in level in response to neuromodulation. For example, a surrogate biomarker may be a catecholamine or metabolite thereof that exhibits a two-fold or greater decrease in a urine sample following neuromodulation. In certain of these embodiments, a surrogate biomarker exhibits a three-fold or greater, five-fold or greater, or ten-fold or greater change in level in response to neuromodulation.

In certain embodiments, surrogate biomarkers for use in the methods disclosed herein exhibit a change in level within a predetermined timeframe post-neuromodulation. In some embodiments, certain surrogate biomarkers for use in the methods disclosed herein may exhibit a change in level relatively contemporaneous to neuromodulation. For example, in certain embodiments a surrogate biomarker exhibits a change in level within 10 minutes, 15 minutes, or 30 minutes of neuromodulation. Accordingly, in certain embodiments, post-neuromodulation level for a surrogate biomarker is determined during neuromodulation or relatively contemporaneous to neuromodulation, i.e., within 10 minutes, 15 minutes, or 30 minutes of neuromodulation. In some embodiments, post-neuromodulation level for a surrogate biomarker is determined in an acute timeframe, i.e., while the subject is still catheterized (e.g., within the renal vasculature) and/or under anesthesia. Alternatively or in addition to a change in level at the time of neuromodulation or relatively contemporaneous to neuromodulation, a surrogate biomarker may exhibit a change in level at a later timepoint (e.g., at a chronic timepoint). For example, in certain embodiments a surrogate biomarker exhibits a change in level within 2 hours, 4 hours, 6 hours, 8 hours, 12 hours, 24 hours, 48 hours, 72 hours, 7 days, 14 days, one month, two months, three months, four months, 6 months or one year of neuromodulation. Accordingly, in certain embodiments, post-neuromodulation level for a surrogate biomarker is determined 2 hours or more after neuromodulation, i.e., within 2 hours, 4 hours, 6 hours, 8 hours, 12 hours, 24 hours, 48 hours, 72 hours, 7 days, 14 days, one month, two months, three months, four months, 6 months, and/or one year of neuromodulation. In certain embodiments, changes in surrogate biomarker level at these later timepoints can be used to assess or classify a subject's response to neuromodulation. The resultant information can be used to develop predictive models for determining whether neuromodulation is likely to be effective in a particular subject or subpopulation. Additionally, the resultant information can be used to determine if a repeat procedure is likely to be effective in a particular subject.

The methods disclosed herein may be used to monitor or assess the efficacy of neuromodulation carried out using a variety of suitable techniques. The neuromodulation, for example, may be electrically-induced, thermally-induced, chemically-induced, or induced in another suitable manner or combination of manners at one or more suitable treatment locations during a treatment procedure. For example, neuromodulation may be carried out by delivering monopolar or bipolar RF energy, microwave energy, laser light or optical energy, magnetic, ultrasound energy (e.g., intravascularly delivered ultrasound, extracorporeal ultrasound, high frequency ultrasound (HIFU)), direct heat energy, and/or cryotherapeutic energy to target tissue at a treatment location to induce one or more desired effects at the treatment location. A treatment location may be a location proximate to one or more nerves being neuromodulated. In some embodiments, the treatment location is in or near a vessel or other body lumen. For example, a treatment location for renal neuromodulation may be at or near the renal artery. In certain embodiments, the identity of the surrogate biomarkers may vary depending on the neuromodulation method being used. For example, neuromodulation using RF energy may result in changes in the level of a different set of surrogate biomarkers than cryotherapy. In other embodiments, a specific surrogate biomarker or set of surrogate biomarkers may be effective for monitoring or assessing efficacy across a range of neuromodulation techniques.

In certain embodiments, changes in surrogate biomarker level can be used in the prognosis of co-morbidities that are directly or indirectly benefited by neuromodulation. In other embodiments, changes in surrogate biomarker level can be used to predict a subject's response to neuromodulation.

Determination of baseline and/or post-neuromodulation surrogate biomarker level may be carried out using any previously known method and/or methods disclosed herein. In some embodiments, for example, determination of surrogate biomarker level utilizes a detection method that produces results in an acute timeframe following neuromodulation. Where a surrogate biomarker is an excreted catecholamine or metabolite thereof, determination of the biomarker level may utilize one or more detection agents.

In certain embodiments, interaction of the surrogate biomarker with a detection agent results in a quantifiable signal. This quantifiable signal may be, for example, a colorimetric, fluorescent, heat, energy, or electric signal. In certain embodiments, this signal may be transduced to an external visual output device. In one particular embodiment high-performance liquid chromatography (HPLC) can be used to identify and quantify one or more surrogate biomarkers in a biological sample. In certain embodiments, a biomarker-specific detection agent may be labeled, such as for example with an enzymatic or radioactive label. A detection agent may be a binding substrate for a secondary capture agent, such as a labeled antibody. In additional embodiments, urine dip-stick tests can be used to rapidly report levels of particular surrogate biomarkers (e.g., albumin, microalbuminuria) present in urine pre- and post-neuromodulation procedures.

In certain embodiments of the methods disclosed herein, determination of baseline and/or post-neuromodulation surrogate biomarker level is carried out using any immunoassay-based method. In one embodiment, enzyme immunoassay (ELISA) techniques can be used to quantify a surrogate biomarker level. In certain examples, surrogate biomarker levels may be determined using an electrochemical immunosensor, which provides concentration-dependent signaling (see, e.g., Centi Bioanalysis 1:1271 (2009); Rusling Analyst 135:2496 (2010)). Antibodies for use in an immunoassay-based determination of surrogate biomarker level may be labeled or unlabeled.

In certain embodiments, the methods provided herein indicate to a practitioner the likelihood that a neuromodulation procedure was successful. For example, the percentage of change of surrogate biomarker level between baseline level and post-neuromodulation level may indicate the level of success of the procedure. In a particular example, a 30%-60%/o decrease in surrogate biomarker level may indicate partial success, while a 70%-90% decrease in surrogate biomarker level may indicate a more desirable efficacy (e.g., complete or near complete success). In some embodiments, the methods provided herein provide a binary "yes or no" indicator of the success of a neuromodulation procedure. In these embodiments, a specific threshold increase or decrease in the level of a surrogate biomarker or set of surrogate biomarkers indicates the neuromodulation procedure was successful. In certain of these embodiments, the specific threshold change indicates that the neuromodulation procedure was successful with a specific confidence interval (e.g., 95% or greater, 97% or greater, or 99% or greater). In some embodiments, information regarding changes in the level of a surrogate biomarker may be combined with one or more additional parameters such as blood pressure, temperature, nerve signaling data, or impedance in assessing neuromodulation efficacy. Further, efficacy may be evaluated based on a combination of all parameters, with changes in surrogate biomarker level simply functioning as one of the parameters.

The following example is provided to better illustrate the disclosed technology and are not to be interpreted as limiting the scope of the technology. To the extent that specific materials are mentioned, it is merely for purposes of illustration and is not intended to limit the technology. It will be understood that many variations can be made in the procedures herein described while still remaining within the bounds of the present technology. It is the intention of the inventors that such variations are included within the scope of the technology.

II. EXPERIMENTAL EXAMPLES

Example 1

This section describes an example of the outcome of renal neuromodulation on animal subjects as assessed by quantification of VMA and NE levels pre- and post-neuromodulation. In this example, and referring to FIG. 1, studies using the pig model have been performed and directed to modulation of nerve tissue at treatment sites within the renal vasculatures using a catheter-based neuromodulation assembly configured to deliver RF energy and commercially available from Medtronic, Inc., of 710 Medtronic Parkway, Minneapolis, Minn. 55432-5604.

Urine samples from eight pigs were collected by urethral catheterization immediately before the renal neuromodulation procedure and 10 minutes (+/−5 minutes) post-neuromodulation and subsequently analyzed. The urine samples were assayed by an ELISA Assay Kit (VMA ELISA Assay Kit commercially available from Eagle Biosciences, Inc., of 20A NW Blvd., Suite 112, Nashua, N.H. 03063).

FIG. 1 is a plot of total combined concentration of VMA and NE (ng/ml) before and after renal neuromodulation procedures and which are plotted as a percent of the pre-neuromodulation (i.e., untreated) control. As shown in FIG. 1, six of eight animals (9644, 9620, 9658, 9617, 9641 and 9637) demonstrated a decrease in combined levels of VMA and NE in approximately 10 minutes following renal neuromodulation treatment. One animal (9621) demonstrated an increase in combined levels of VMA and NE following renal neuromodulation, and one animal (9646) showed no significant difference in combined levels of VMA and NE following renal neuromodulation.

These findings suggest that systemic urine samples assessed for levels of catecholamines (e.g., NE) and metabolites thereof (e.g., VMA) may be used to assess efficacy of renal neuromodulation and/or predict a level of success of a renal neuromodulation procedure post-treatment in the patient. Renal neuromodulation is known to result in cohorts of different levels of responders to the treatment and/or accuracy of targeted nerve ablation. For example, in some human patients and porcine animal experiments, some subjects have no change in blood pressure or other clinical symptoms or measurable physiological parameters associated with hypertension and this is correlated with poor denervation of targeted nerve tissue (upon histological analysis of animal subjects). In other human patients and porcine animal experiments, some subjects have partial improvement (e.g., 30%-60% improvement) in blood pressure or other clinical symptoms or measurable physiological parameters associated with hypertension and this is correlated with partial denervation of targeted nerve tissue (upon histological analysis of animal subjects). Additionally, in many human patients and porcine animal experiments, subjects have significant improvement in blood pressure or other clinical symptoms or measurable physiological parameters associated with hypertension and this is correlated with significant denervation of targeted nerve tissue (upon histological analysis of animal subjects). Without being bound by theory, it is hypothesized that animals demonstrating significant reduction in VMA and NE levels in urine collected post-neuromodulation correlate with significant and/or sufficient denervation of targeted nerve tissue, or in cases of modest reduction (e.g., animal 9637), with partial denervation of targeted nerve tissue. Further, animals demonstrating an increase or no significant reduction in VMA and NE levels in urine collected post-neuromodulation may correlate with insufficient denervation of targeted nerve tissue.

Example 2

Example 2 describes the effect of renal neuromodulation on components of the RAAS in human patients with resistant hypertension. Eight patients (55.4±13 years) with treatment resistant hypertension were included in a study to determine blood and urine samples levels of individual components of the renin-angiotensin-aldosterone system (RAAS) before (day −1), after (day=1) and again after 3 months of renal nerve ablation.

Results indicated no statistically significant change in renal plasma flow, plasma renin activity or serum angiotensin II levels in this cohort of patients. There was a significant acute decrease in plasma aldosterone concentration one day post ablation (day −1:161 (140-265) vs. day +1:110 (101-168) pg/ml, p=0.012) and in accordance an increased urinary sodium/potassium ratio (day −1:2.41 (1.17-3.44) vs. day +1:6.02 (4.83-7.92), p=0.028). After 3 months, these changes were no longer evident. Urinary angiotensinogen levels, considered as a parameter of the local renal RAAS activity, tended to be reduced at day +1 (P=0.116) and significantly decreased after 3 months (6.06 (3.02-13.8) vs. 16.6 (8.50-37.0). P=0.046 compared to day −1 levels.

Example 3

Example 3 describes a method of assessing the outcome of renal neuromodulation on animal subjects by quantification of renin and aldosterone concentration levels in plasma pre- and post-neuromodulation. In this example, studies using the pig model will be performed and directed to modulation of nerve tissue at treatment sites within the renal vasculatures using a catheter-based neuromodulation assembly configured to deliver RF energy and commercially available from Medtronic, Inc., of Minneapolis, Minn. Serum samples from each animal will collected pre-neuromodulation, approximately 15 minutes post-neuromodulation, and 28 days post-neuromodulation.

Protein concentration levels of systemic renin and systemic aldosterone will be assessed for each animal pre-neuromodulation and post-neuromodulation at 10 min+/−5 min (acute time-frame), 14 days post-neuromodulation, and 28 days post-neuromodulation using standard ELISA techniques. For example, serum samples will be assayed for pig renin protein levels by an ELISA Assay Kit (Pig Renin ELISA Kit commercially available from Cusabio® Biotech Company, Ltd., of Wuhan, Hubei Province 430206, P.R. China). Serum samples will also be assayed for pig aldosterone protein levels by an ELISA Assay Kit (Aldosterone (Pig) ELISA kit commercially available from Abnova Corporation of Neihu District. Taipei City 114 Taiwan).

In addition to quantification of systemic renin and aldosterone protein concentration levels in serum at the selected time points pre- and post-neuromodulation, the animals will be assessed for blood pressure (e.g., office blood pressure measurements) at the selected time points, as well as by telemetry (e.g., ambulatory blood pressure measurements) during the course of the study. Animals will be sacrificed on day 28 and cortical axon density (i.e., cortical axon area (per $mm^2$)) will be assessed. The study will allow an investigator to determine the trend (e.g., increased levels, decreased levels, spikes in levels, etc.) of systemic renin and aldosterone protein concentrations following renal denervation and assess such concentration levels as a predictor (e.g., surrogate biomarker) of procedural efficacy (e.g., as level changes correlate with decrease(s) in office and telemetry blood pressure readings and cortical axon density measurements). The results of this study may be used to assess the predictive value of systemic renin and aldosterone levels in serum as an immediate (e.g., within 15 minutes post-neuromodulation) or long-term (e.g., within 28 days post-neuromodulation) predictor of efficacy of renal neuromodulation and/or predictor of a level of success of a renal neuromodulation procedure post-treatment in the patient.

As discussed above, renal neuromodulation is known to result in cohorts of different levels of responders to the treatment and/or accuracy of targeted nerve ablation: (a) those with no long-term change in blood pressure or other clinical symptoms or measurable physiological parameters associated with hypertension which is correlated with poor denervation of targeted nerve tissue (upon histological analysis of animal subjects); (b) those partial improvement (e.g., 30%-60% improvement) in blood pressure or other clinical symptoms or measurable physiological parameters associated with hypertension which is correlated with partial denervation of targeted nerve tissue (upon histological analysis of animal subjects); and (c) those demonstrating significant improvement in blood pressure or other clinical symptoms or measurable physiological parameters associated with hypertension that is correlated with significant denervation of targeted nerve tissue (upon histological analysis of animal subjects).

Without being bound by theory, it is hypothesized that animals demonstrating immediate and/or long-term changes in levels of systemic renin and/or aldosterone in serum collected post-neuromodulation will be a correlative predictor for significant and/or sufficient ablation of targeted nerve tissue, or in cases of modest immediate and/or long-term changes, with partial denervation of targeted nerve tissue. Further, animals demonstrating no significant change in renin and/or aldosterone levels in urine collected post-neuromodulation may correlate with insufficient ablation of targeted nerve tissue. As such, systemic renin and/or aldosterone levels in serum collected from patients post-neuromodulation may indicate to a treating physician the degree (within predictive tolerances) of renal denervation achieved for assessing treatment success and/or the value of a repeat procedure to meet therapeutic benchmarks in individual patients.

III. SELECTED EMBODIMENTS OF RENAL NEUROMODULATION SYSTEMS AND DEVICES

Figure 2:
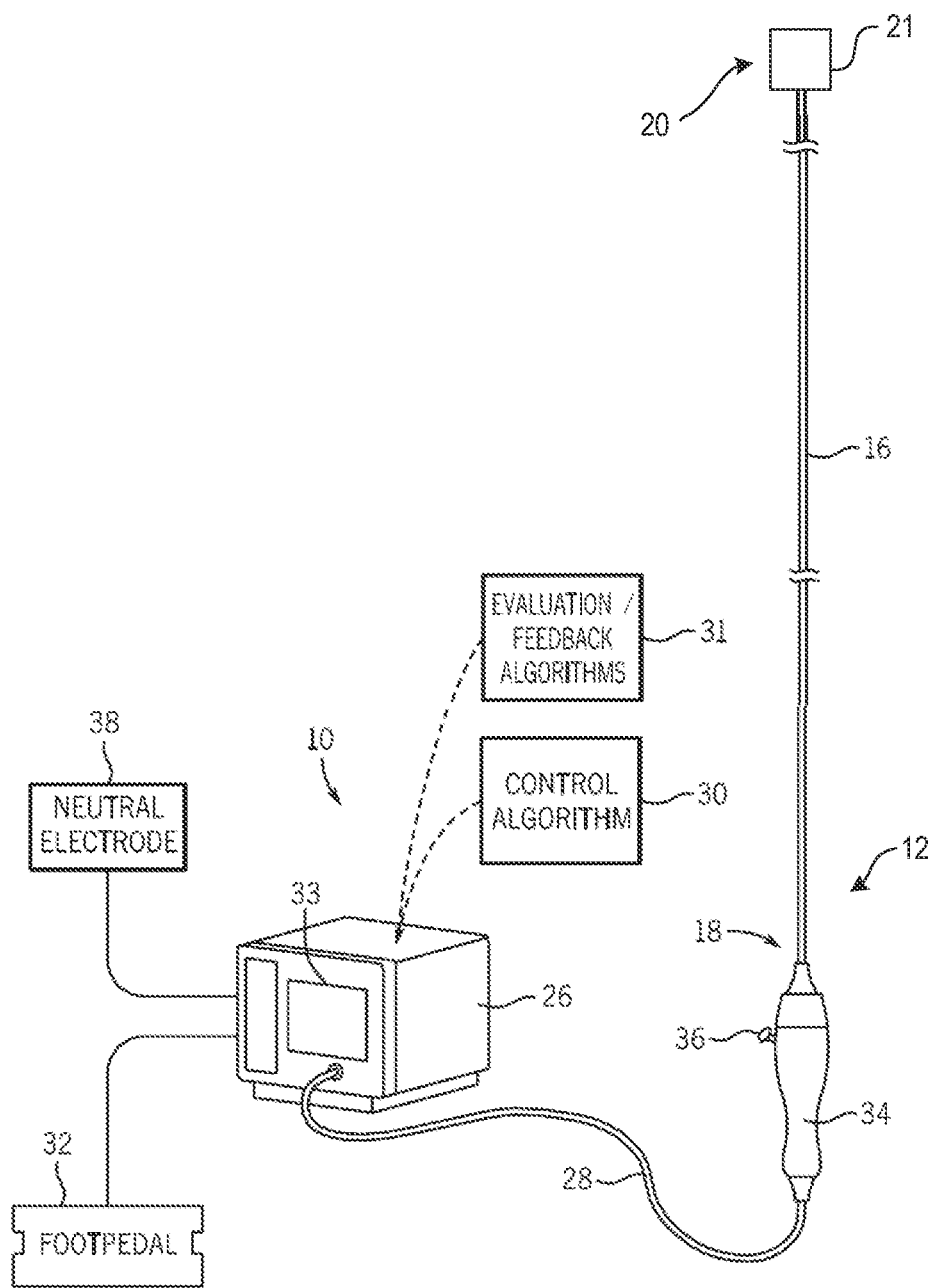
FIG. 2 illustrates an intravascular neuromodulation system configured in accordance with an embodiment of the present technology.

FIG. 2 illustrates a renal neuromodulation system 10 configured in accordance with an embodiment of the present technology. The system 10, for example, may be used to perform therapeutically-effective renal neuromodulation on a patient diagnosed with increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, and osteoporosis, among others. The system 10 includes an intravascular treatment device 12 operably coupled to an energy source or console 26 (e.g., a RF energy generator, a cryotherapy console). In the embodiment shown in FIG. 2, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a neuromodulation assembly or treatment section 21 at the distal portion 20 of the shaft 16. The neuromodulation assembly 21 can be configured to ablate nerve tissue and/or for monitoring one or more physiological parameters within the vasculature. Accordingly, a neuromodulation assembly 21 suitable for ablation may include one or more electrodes, transducers, energy-delivery elements or cryotherapeutic cooling assemblies. Neuromodulation assemblies 21 suitable for monitoring may include a nerve monitoring device and/or blood collection/analysis device. In some embodiments, the neuromodulation assembly 21 can be configured to be delivered to a renal blood vessel (e.g., a renal artery) in a low-profile configuration.

In one embodiment, for example, the neuromodulation assembly 21 can include a single electrode. In other embodiments, the neuromodulation assembly 21 may comprise a basket and a plurality of electrodes carried by the basket. The electrodes on the basket may be spaced apart from each other such that each electrode is approximately 90° apart from a neighboring electrode. In yet another embodiment, the neuromodulation assembly 21 can include a balloon and a plurality of bipolar electrodes carried by the balloon. In still another embodiment, the neuromodulation assembly 21 has a plurality of electrodes arranged along an elongated member transformable between a low-profile, delivery configuration (e.g., contained in a delivery catheter) and an expanded, deployed configuration in which the elongated member has a helical/spiral shape. In further embodiments, the neuromodulation assembly 21 can include one or more electrodes configured to deliver ablation energy and/or stimulation energy. In some arrangements, the neuromodulation assembly 21 can include one or more sensor(s) for detecting impedance or nerve monitoring signals. In any of the foregoing embodiments, the neuromodulation assembly 21 may comprise an irrigated electrode.

Upon delivery to a target treatment site within a renal blood vessel, the neuromodulation assembly 21 can be further configured to be deployed into a treatment state or arrangement for delivering energy at the treatment site and providing therapeutically-effective electrically-induced and/or thermally-induced renal neuromodulation. In some embodiments, the neuromodulation assembly 21 may be placed or transformed into the deployed state or arrangement via remote actuation, e.g., via an actuator 36, such as a knob, pin, or lever carried by the handle 34. In other embodiments, however, the neuromodulation assembly 21 may be transformed between the delivery and deployed states using other suitable mechanisms or techniques.

The proximal end of the neuromodulation assembly 21 can be carried by or affixed to the distal portion 20 of the elongated shaft 16. A distal end of the neuromodulation assembly 21 may terminate with, for example, an atraumatic rounded tip or cap. Alternatively, the distal end of the neuromodulation assembly 21 may be configured to engage another element of the system 10 or treatment device 12. For example, the distal end of the neuromodulation assembly 21 may define a passageway for engaging a guide wire (not shown) for delivery of the treatment device using over-the-wire ("OTW") or rapid exchange ("RX") techniques. The treatment device 12 can also be a steerable or non-steerable catheter device (e.g., a guide catheter) configured for use without a guide wire. Body lumens (e.g., ducts or internal chambers) can be treated, for example, by non-percutaneously passing the shaft 16 and neuromodulation assembly 21 through externally accessible passages of the body or other suitable methods.

The console 26 can be configured to generate a selected form and magnitude of energy for delivery to the target treatment site via the neuromodulation assembly 21. A control mechanism, such as a foot pedal 32, may be connected (e.g., pneumatically connected or electrically connected) to the console 26 to allow an operator to initiate, terminate and, optionally, adjust various operational characteristics of the console 26, including, but not limited to, power delivery. The system 10 may also include a remote control device (not shown) that can be positioned in a sterile field and operably coupled to the neuromodulation assembly 21. The remote control device can be configured to allow for selective activation of the neuromodulation assembly 21. In other embodiments, the remote control device may be built into the handle assembly 34. The energy source 26 can be configured to deliver the treatment energy via an automated control algorithm 30 and/or under the control of the clinician. In addition, the energy source 26 may include one or more evaluation or feedback algorithms 31 to provide feedback to the clinician before, during, and/or after therapy.

The energy source 26 can further include a device or monitor that may include processing circuitry, such as a microprocessor, and a display 33. The processing circuitry may be configured to execute stored instructions relating to the control algorithm 30. The energy source 26 may be configured to communicate with the treatment device 12 (e.g., via a cable 28) to control the neuromodulation assembly and/or to send signals to or receive signals from the nerve monitoring device. The display 33 may be configured to provide indications of power levels or sensor data, such as audio, visual or other indications, or may be configured to communicate information to another device. For example, the console 26 may also be configured to be operably coupled to a catheter lab screen or system for displaying treatment information, such as nerve activity before and/or after treatment.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or balloon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

IV. SELECTED EXAMPLES OF TREATMENT PROCEDURES FOR RENAL NEUROMODULATION

Figure 3:
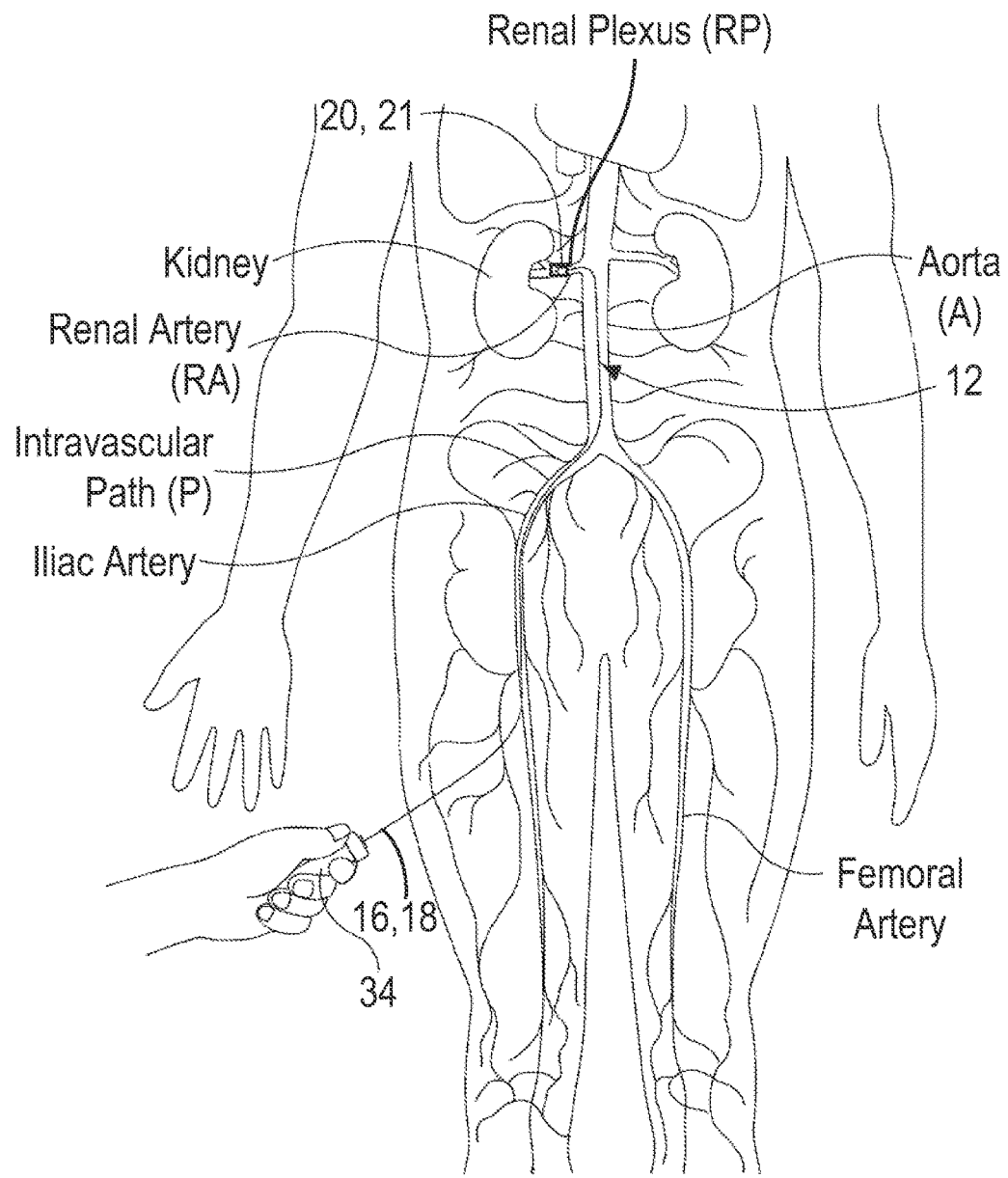
FIG. 3 illustrates modulating renal nerves with a neuromodulation system configured in accordance with an embodiment of the present technology.

FIG. 3 illustrates modulating renal nerves with an embodiment of the system 10 (FIG. 2). The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12. In some embodiments, the shaft 16 and the neuromodulation assembly 21 can be 3, 4, 5, 6, or 7 French or another suitable size. Furthermore, the shaft 16 and the neuromodulation assembly 21 can be partially or fully radiopaque and/or can include radiopaque markers corresponding to measurements, e.g., every 5 cm.

After the neuromodulation assembly 21 is adequately positioned in the renal artery RA, it can be radially expanded or otherwise deployed using the handle 34 or other suitable control mechanism until the neuromodulation assembly is positioned at its target site and in stable contact with the inner wall of the renal artery RA. The purposeful application of energy from the neuromodulation assembly can then be applied to tissue to induce one or more desired neuromodulating effects on localized regions of the renal artery RA and adjacent regions of the renal plexus RP, which lay intimately within, adjacent to, or in close proximity to the adventitia of the renal artery RA. The neuromodulating effects may include denervation, thermal ablation, and non-ablative thermal alteration or damage (e.g., via sustained heating and/or resistive heating). The purposeful application of the energy may achieve neuromodulation along all or at least a portion of the renal plexus RP.

In the deployed state, the neuromodulation assembly 21 can be configured to contact an inner wall of a vessel of the renal vasculature and to form a suitable lesion or pattern of lesions without the need for repositioning. For example, the neuromodulation assembly 21 can be configured to form a single lesion or a series of lesions, e.g., overlapping and/or non-overlapping. In some embodiments, the lesion(s) (e.g., pattern of lesions) can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the neuromodulation assembly 21 can be configured form a partially-circumferential lesion or a fully-circumferential lesion at a single longitudinal segment or zone of the vessel. During treatment, the neuromodulation assembly 21 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the neuromodulation assembly 21 can be configured to cause therapeutically-effective neuromodulation (e.g., using ultrasound energy) without contacting a vessel wall.

As mentioned previously, the methods disclosed herein may use a variety of suitable energy modalities, including RF energy, pulsed RF energy, microwave energy, laser, optical energy, ultrasound energy (e.g., intravascularly delivered ultrasound, extracorporeal ultrasound, HIFU), magnetic energy, direct heat, cryotherapy, radiation (e.g., infrared, visible, gamma), or a combination thereof. Alternatively or in addition to these techniques, the methods may utilize one or more non-ablative neuromodulatory techniques. For example, the methods may utilize non-ablative SNS neuromodulation by removal of target nerves (e.g., surgically), injection of target nerves with a destructive drug or pharmaceutical compound, or treatment of the target nerves with non-ablative energy modalities (e.g., laser or light energy). In certain embodiments, the amount of reduction of the sympathetic nerve activity may vary depending on the specific technique being used.

Furthermore, a treatment procedure can include treatment at any suitable number of treatment locations, e.g., a single treatment location, two treatment locations, or more than two treatment locations. In some embodiments, different treatment locations can correspond to different portions of the renal artery RA, the renal vein, and/or other suitable structures proximate tissue having relatively high concentrations of renal nerves. The shaft 16 can be steerable (e.g., via one or more pull wires, a steerable guide or sheath catheter, etc.) and can be configured to move the neuromodulation assembly 21 between treatment locations. At each treatment location, the neuromodulation assembly 21 can be activated to cause modulation of nerves proximate the treatment location. Activating the neuromodulation assembly 21 can include, for example, heating, cooling, stimulating, or applying another suitable treatment modality at the treatment location. Activating the neuromodulation assembly 21 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the neuromodulation assembly 21 can be configured to introduce (e.g., inject) a chemical (e.g., a drug or other agent) into target tissue at the treatment location. Such chemicals or agents can be applied at various concentrations depending on treatment location and the relative depth of the target nerves.

As discussed, the neuromodulation assembly 21 can be positioned at a treatment location within the renal artery RA, for example, via a catheterization path including a femoral artery and the aorta, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The neuromodulation assembly 21 can be configured to accommodate the anatomy of the renal artery RA, the renal vein, and/or another suitable structure. For example, the neuromodulation assembly 21 can include a balloon (not shown) configured to inflate to a size generally corresponding to the internal size of the renal artery RA, the renal vein, and/or another suitable structure. In some embodiments, the neuromodulation assembly 21 can be an implantable device and a treatment procedure can include locating the neuromodulation assembly 21 at the treatment location using the shaft 16 fixing the neuromodulation assembly 21 at the treatment location, separating the neuromodulation assembly 21 from the shaft 16, and withdrawing the shaft 16. Other treatment procedures for modulation of renal nerves in accordance with embodiments of the present technology are also possible.

V. FURTHER EXAMPLES

The following examples are illustrative of several embodiments of the present technology:

1. A method of assessing the efficacy of a renal neuromodulation procedure in a human subject, the method comprising:
   determining a baseline level of one or more biomarkers in plasma or urine collected from the human subject;
   at least partially inhibiting sympathetic neural activity in a renal nerve of the human subject via a neuromodulation assembly;
   determining a post-neuromodulation level for the biomarker(s) in plasma or urine collected from the human subject; and
   comparing the post-neuromodulation level to the baseline level, wherein the neuromodulation procedure is classified as at least partially successful if the post-neuromodulation level differs significantly from the baseline level.

2. The method of example 1 wherein the one or more biomarkers includes a catecholamine or a metabolite thereof.

3. The method of example 1 or example 2 wherein the one or more biomarkers includes norepinephrine.

4. The method of any one of examples 1-3 wherein the one or more biomarkers includes vanillylmandelic acid in urine collected from the human subject.

5. The method of any one of examples 1-4 wherein determining a baseline level of one or more biomarkers includes determining a baseline level of norepinephrine and vanillylmandelic acid in urine collected from the human subject, and wherein determining a post-neuromodulation level for the biomarker(s) includes determining a post-neuromodulation level of norepinephrine and vanillylmandelic acid in urine collected from the human subject.

6. The method of any one of examples 1-4 wherein the one or more biomarkers includes neuropeptide Y in plasma collected from the human subject.

7. The method of any one of examples 1-4 and example 6 wherein the one or more biomarkers includes vasopressin collected in plasma collected from the human subject.

8. The method of example 1 wherein the one or more biomarkers includes total catecholamines and metabolites thereof in urine collected from the human subject.

9. The method of example 1 wherein the one or more biomarkers is selected from the group consisting of norepinephrine, normetanephrine, vanillylmandelic acid, epinephrine, metanephrine, neuropeptide Y, vasopressin, albumin and microalbuminuria.

10. The method of example 1 wherein the one or more biomarkers is selected from a component of the renin-angiotensin aldosterone system in plasma collected from the human subject.

11. The method of example 10 wherein the component of the renin-angiotensin aldosterone system is aldosterone.

12. The method of any one of examples 1-11 wherein the baseline level is significantly higher than the post-neuromodulation level.

13. The method of any one of examples 1-12 wherein the post-neuromodulation level is at least about 20%, about 30%, or about 40% lower than the baseline level.

14. The method of any one of examples 1-13 wherein the post neuromodulation level is at least about 50% lower than the baseline level.

15. The method of any one of examples 1-14 wherein the post neuromodulation level is at least about 50%, about 60% or about 70% lower than the baseline level.

16. The method of any one of examples 1-15 wherein the post neuromodulation level is at least about 80% or about 90% lower than the baseline level. 17. The method of any one of examples 1-16 wherein the post-neuromodulation level of the biomarker(s) is determined at about 15 minutes, about 24 hours, or about 7 days post-denervation.

18. The method of any one of examples 1-16 wherein the post-neuromodulation level of the biomarker(s) is determined at about 1 month, 3 months or about 6 months post-denervation.

19. The method of any one of examples 1-11 wherein the baseline level is significantly lower than the post-neuromodulation level, and wherein the post-neuromodulation level of the biomarker(s) is determined at about 15 minutes or about 24 hours post-denervation.

20. The method of example 19 wherein a post-neuromodulation level of the biomarker(s) determined at about 1 month, about 3 months, or about 6 months post-denervation is lower than the baseline level and the level determined at about 15 minutes or about 24 hours post-denervation.

21. The method of any one of examples 1-20 wherein at least partially inhibiting sympathetic neural activity in a renal nerve of the human subject comprises delivering energy to the renal nerve via the neuromodulation assembly to modulate the renal nerve.

22. The method of example 21 wherein the energy is radio frequency (RF) energy.

23. The method of example 21 wherein the energy is selected from the group consisting of pulsed RF energy, microwave energy, laser light energy, optical energy, ultrasound energy, high-intensity focused ultrasound energy, magnetic energy, direct heat energy, and cryotherapeutic energy.

24. The method of any one of examples 1-22 wherein the neuromodulation assembly comprises an intravascularly positioned catheter carrying an energy delivery element positioned at least proximate to the renal nerve.

25. The method of any one of examples 1-22 wherein at least partially inhibiting sympathetic neural activity in a renal nerve of the human subject comprises thermally modulating the renal nerve via the neuromodulation assembly from within a renal blood vessel of the subject.

26. A method of assessing efficacy of a renal neuromodulation procedure in a human subject, the method comprising:
    determining a post-neuromodulation level for one or more biomarker(s) in plasma or urine collected from the human subject following the renal neuromodulation procedure, wherein the level of biomarker(s) directly or indirectly correlate with sympathetic nervous activity in the human subject; and
    comparing the post-neuromodulation level to a pre-determined threshold level for the biomarker(s), wherein the renal neuromodulation procedure is classified as at least partially successful if the post-neuromodulation level is less than the pre-determined threshold level.

27. A method of assessing efficacy of a renal neuromodulation procedure in a human subject, the method comprising:
    determining a post-neuromodulation level for one or more biomarker(s) in plasma or urine collected from the human subject following the renal neuromodulation procedure, wherein the level of biomarker(s) directly or indirectly correlate with sympathetic nervous activity in the human subject; and
    comparing the post-neuromodulation level to a pre-determined range of level for the biomarker(s), wherein the renal neuromodulation procedure is classified as at least partially successful if the post-neuromodulation level falls within or near the pre-determined range of level.

28. The method of example 26 or example 27 wherein the one or more biomarker(s) includes a catecholamine or a metabolite thereof.

29. The method of any one of examples 26-28 wherein the one or more biomarkers includes norepinephrine.

30. The method of any one of examples 26-29 wherein the one or more biomarkers includes vanillylmandelic acid in urine collected from the human subject.

31. The method of example 26 or example 27 wherein the one or more biomarkers is selected from the group consisting of norepinephrine, normetanephrine, vanillylmandelic acid, epinephrine, metanephrine, neuropeptide Y, vasopressin and albumin.

32. The method of example 26 or example 27 wherein the one or more biomarkers is selected from a component of the renin-angiotensin aldosterone system in plasma collected from the human subject.

33. The method of example 32 wherein the component of the renin-angiotensin aldosterone system is aldosterone.

34. The method of any one of examples 26-33 wherein before determining a post-neuromodulation level for one or more biomarker(s), the method further comprises at least partially inhibiting sympathetic neural activity in a renal nerve of the human subject via a neuromodulation assembly.

35. The method of any one of examples 26-33 wherein prior to determining a post neuromodulation level for the biomarkers, the method further comprises:
    transluminally positioning an energy delivery element of a catheter within a target blood vessel of the human subject and adjacent to target neural fibers; and
    at least partially ablating the target neural fibers via the energy delivery element.

36. The method of any one of examples 26-29 wherein the post-neuromodulation level of the biomarker(s) is determined at about 15 minutes, about 24 hours, or about 7 days following the renal neuromodulation procedure.

37. The method of any one of examples 26-35 wherein the post-neuromodulation level of the biomarker(s) is determined at about 1 month, 3 months or about 6 months following the renal neuromodulation procedure.

38. The method of any one of examples 26 and 28-37 wherein the pre-determined threshold level is an upper limit of a normal range of level for the biomarker(s).

39. The method of any one of examples 27-37 wherein the pre-determined range of level for the biomarker(s) is a normal range of level for the biomarker(s).

40. The method of example 26 or example 27 wherein the level of biomarker(s) directly or indirectly correlate with blood pressure in the human subject.

41. A device for carrying out the method of any of examples 1-40.

42. A system for carrying out the method of any of examples 1-40.

VI. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of assessing efficacy of a renal neuromodulation procedure in a human patient, the method comprising:
   selecting one or more biomarkers indicative of a level of sympathetic nervous activity or blood pressure from a group consisting of normetanephrine, vanillylmandelic acid, metanephrine, and homovanillic acid;
   determining a baseline level of the one or more biomarkers in urine collected from the human patient;
   at least partially inhibiting sympathetic neural activity in a renal nerve of the human patient via a neuromodulation assembly;
   determining a post-neuromodulation level of the one or more biomarkers in urine collected from the human patient;
   calculating a difference value between the post-neuromodulation level and the baseline level of the one or more biomarkers in the urine; and
   classifying the renal neuromodulation procedure as at least partially successful when the difference value is between a first threshold value and a second threshold value, and as completely successful when the difference value is greater than the second threshold value, wherein the first threshold value is determined from differences between post-neuromodulation levels and baseline levels achieved by patients having previously undergone partially successful renal neuromodulation, and wherein the second threshold value is determined from differences between post-neuromodulation levels and baseline levels achieved by patients having previously undergone completely successful renal modulation.

2. The method of claim 1 wherein the one or more biomarkers comprises vanillylmandelic acid in urine collected from the human patient.

3. The method of claim 1 wherein:
   determining the baseline level of the one or more biomarkers includes determining a baseline level of norepinephrine and vanillylmandelic acid in urine collected from the human patient; and
   determining the post-neuromodulation level of the one or more biomarkers includes determining a post-neuromodulation level of norepinephrine and vanillylmandelic acid in urine collected from the human patient.

4. The method of claim 1 wherein the urine for determining the post-neuromodulation level is collected from the human patient prior to removing the neuromodulation assembly from the human patient.

5. The method of claim 1 wherein:
   determining the baseline level of the one or more biomarkers includes determining a baseline level of norepinephrine and normetanephrine in urine collected from the human patient; and
   determining the post-neuromodulation level of the one or more biomarkers includes determining a post-neuromodulation level of norepinephrine and normetanephrine in urine collected from the human patient.

6. The method of claim 1 wherein:
   determining the baseline level of the one or more biomarkers includes determining a baseline level of epinephrine and one or both of metanephrine and vanillymandelic acid in urine collected from the human patient; and
   determining a post-neuromodulation level of the one or more biomarkers includes determining a post-neuromodulation level of epinephrine and one or both of metanephrine and vanillymandelic acid in urine collected from the human patient.

7. The method of claim 1 wherein:
   determining the baseline level of the one or more biomarkers includes determining a baseline level of dopamine and homovanillic acid in urine collected from the human patient; and
   determining a post-neuromodulation level of the one or more biomarkers includes determining a post-neuromodulation level of dopamine and homovanillic acid in urine collected from the human patient.

8. The method of claim 1 wherein the post-neuromodulation level is a first post-neuromodulation level, and wherein the method further comprises:
   determining a second post-neuromodulation level of the one or more biomarkers at about 1 month post-neuromodulation, and
   wherein the second post-neuromodulation level is lower than the baseline level and the first post-neuromodulation level.

9. The method of claim 1 wherein the urine for determining the post-neuromodulation level is collected from the human patient within about 10 minutes post-neuromodulation.

10. The method of claim 1 wherein the urine for determining the post-neuromodulation level is collected from the human patient at one or more time points over 24 hours post-neuromodulation.

11. The method of claim 1 wherein the post-neuromodulation level is at least about 20% lower than the baseline level.

12. The method of claim 1 wherein the post-neuromodulation level is at least about 60% lower than the baseline level.

13. The method of claim 1 wherein the difference between the baseline level and the post-neuromodulation level corresponds to a degree of ablation of the renal nerve.

14. The method of claim 1 wherein the first threshold value is determined from an average of the differences between the post-neuromodulation levels and the baseline levels achieved by patients having previously undergone partially successful renal neuromodulation, wherein the second threshold value is determined from an average of the differences between the post-neuromodulation levels and the baseline levels achieved by patients having previously undergone completely successful renal neuromodulation.

15. A method of assessing efficacy of a renal neuromodulation procedure in a human patient, the method comprising:

selecting one or more biomarkers indicative of a level of sympathetic nervous activity or blood pressure from a group consisting of normetanephrine, vanillylmandelic acid, metanephrine, and homovanillic acid;

determining a baseline level of the one or more biomarkers in urine collected from the human patient;

at least partially inhibiting sympathetic neural activity in a renal nerve of the human patient via a neuromodulation assembly;

determining a post-neuromodulation level of the one or more biomarkers in urine collected from the human patient;

determining a difference between the post-neuromodulation level and the baseline level of the one or more biomarkers in the urine; and classifying the renal neuromodulation procedure as at least partially successful when the difference is between a first threshold amount and a second threshold amount, and as completely successful when the difference is greater than the second threshold amount, wherein the first threshold amount is based on post-neuromodulation levels and baseline levels achieved by patients having previously undergone partially successful renal neuromodulation, and wherein the second threshold amount is based on post-neuromodulation levels and baseline levels achieved by patients having previously undergone completely successful renal modulation;

wherein the first threshold amount is based on an average of the differences between the post-neuromodulation levels and the baseline levels achieved by patients having previously undergone partially successful renal neuromodulation, wherein the second threshold amount is based on an average of the differences between the post-neuromodulation levels and the baseline levels achieved by patients having previously undergone completely successful renal neuromodulation.

* * * * *